United States Patent [19]
McGarry et al.

[11] Patent Number: 5,382,254
[45] Date of Patent: Jan. 17, 1995

[54] ACTUATING HANDLE FOR SURGICAL INSTRUMENTS

[75] Inventors: Richard A. McGarry, Norwalk; Paul J. Phillips, Middlebury; Giovanni Gonzalez, Norwalk; Salvatore Castro, Seymour, all of Conn.

[73] Assignee: United States Surgical Corporation, Norwalk, Conn.

[21] Appl. No.: 969,754

[22] Filed: Oct. 30, 1992

Related U.S. Application Data

[60] Continuation-in-part of Ser. No. 939,029, Sep. 2, 1992, abandoned, which is a continuation of Ser. No. 794,492, Nov. 19, 1991, abandoned, which is a division of Ser. No. 530,652, May 30, 1990, Pat. No. 5,084,057, which is a continuation-in-part of Ser. No. 381,265, Jul. 18, 1989, Pat. No. 5,100,420.

[51] Int. Cl.$^6$ .............................................. A61B 17/04
[52] U.S. Cl. ..................................... 606/143; 606/142
[58] Field of Search .................. 606/139, 143, 142; 227/19, 175–182

[56] References Cited

U.S. PATENT DOCUMENTS

| | | |
|---|---|---|
| D. 276,650 | 12/1984 | Green et al. . |
| 2,008,367 | 7/1935 | Rhinevault . |
| 2,741,248 | 4/1956 | Woodhall . |
| 2,968,041 | 1/1961 | Skold . |
| 3,585,985 | 6/1971 | Gould . |
| 3,603,310 | 9/1971 | Mottin et al. . |
| 3,631,707 | 1/1972 | Miller . |
| 3,777,538 | 12/1973 | Weatherly et al. . |
| 3,834,392 | 9/1974 | Lampman et al. . |
| 3,848,773 | 11/1974 | Adler et al. . |
| 3,856,016 | 12/1974 | Davis . |
| 3,870,048 | 3/1975 | Yoon . |
| 3,882,854 | 5/1975 | Hulka et al. . |
| 3,954,108 | 5/1976 | Davis . |
| 3,955,581 | 5/1976 | Spasiano et al. . |
| 3,989,049 | 11/1976 | Yoon . |
| 4,027,510 | 6/1977 | Hiltebrandt . |
| 4,038,987 | 8/1977 | Komiya . |
| 4,064,881 | 12/1977 | Meredith . |
| 4,084,594 | 4/1978 | Mosior . |

(List continued on next page.)

FOREIGN PATENT DOCUMENTS

| | | |
|---|---|---|
| 0406724 | 1/1991 | European Pat. Off. . |
| 0409569 | 1/1991 | European Pat. Off. . |
| 0507537 | 7/1992 | European Pat. Off. . |
| 0510826 | 10/1992 | European Pat. Off. . |
| 2330182 | 1/1975 | Germany . |
| 2546696 | 4/1976 | Germany . |
| 3802651 | 8/1989 | Germany . |
| 49-29110 | 3/1974 | Japan . |
| 2054384 | 7/1979 | United Kingdom . |
| 2070499 | 9/1981 | United Kingdom . |
| 1093329 | 5/1984 | U.S.S.R. . |
| 8910094 | 11/1989 | WIPO . |
| 9003763 | 4/1990 | WIPO . |

OTHER PUBLICATIONS

Richard Wolf Instruction Manual, "Laparoscopic Sterilization with Spring Clips," by Jaroslav F. Hulka, M. D.

Information Booklet for Auto Suture ® Premium Surgiclip ™ Titanium Disposable Automatic Clip Appliers.

(List continued on next page.)

*Primary Examiner*—Stephen C. Pellegrino
*Assistant Examiner*—Gary Jackson

[57] ABSTRACT

An apparatus is disclosed for individually applying surgical clips endoscopically to body tissue which includes a frame, an elongated endoscopic section having clip closing jaws positioned at a distal end thereof and surgical clips slidably positioned therein, rotatably connected to a distal end of the frame such that the endoscopic section extends distally therefrom. The apparatus includes a system for individually advancing the surgical clips into the clip closing jaws and a system for closing the clip closing jaws. An interference mechanism is associated with the a release mechanism, and is configured, dimensioned and adapted to prevent actuation of the jaw closing system until a surgical clip is positioned between the clip closing jaws.

9 Claims, 18 Drawing Sheets

U.S. PATENT DOCUMENTS

| | | |
|---|---|---|
| 4,085,743 | 4/1978 | Yoon . |
| 4,101,063 | 7/1978 | Kapitanov et al. . |
| 4,103,680 | 8/1978 | Yoon . |
| 4,152,920 | 5/1979 | Green . |
| 4,166,466 | 9/1979 | Jarvik . |
| 4,169,476 | 10/1979 | Hiltebrandt . |
| 4,185,762 | 1/1980 | Froehlich . |
| 4,188,953 | 2/1980 | Klieman et al. . |
| 4,196,836 | 4/1980 | Becht . |
| 4,226,239 | 10/1980 | Polk et al. . |
| 4,226,242 | 10/1980 | Jarvik . |
| 4,228,895 | 10/1980 | Larkin . |
| 4,230,116 | 10/1980 | Watson . |
| 4,240,411 | 12/1980 | Hosono . |
| 4,242,902 | 1/1981 | Green . |
| 4,246,903 | 1/1981 | Larkin . |
| 4,257,419 | 3/1981 | Göltner et al. . |
| 4,273,129 | 6/1981 | Boebel . |
| 4,296,751 | 10/1981 | Blake, III et al. . |
| 4,299,224 | 11/1981 | Noiles . |
| 4,316,468 | 2/1982 | Klieman et al. . |
| 4,325,376 | 4/1982 | Klieman et al. . |
| 4,325,377 | 4/1982 | Boebel . |
| 4,335,928 | 6/1982 | Barrett et al. . |
| 4,338,947 | 7/1982 | Williams . |
| 4,367,746 | 1/1983 | Derechinsky . |
| 4,372,316 | 2/1983 | Blake, III et al. . |
| 4,374,523 | 2/1983 | Yoon . |
| 4,393,883 | 7/1983 | Smyth et al. . |
| 4,412,539 | 11/1983 | Jarvik . |
| 4,425,915 | 1/1984 | Ivanov . |
| 4,430,997 | 2/1984 | DiGiovanni et al. . |
| 4,440,170 | 4/1984 | Golden et al. . |
| 4,450,839 | 5/1984 | Transue . |
| 4,452,357 | 6/1984 | Klieman et al. . |
| 4,452,376 | 6/1984 | Klieman et al. . |
| 4,471,780 | 9/1984 | Menges et al. . |
| 4,479,489 | 10/1984 | Tucci . |
| 4,480,641 | 11/1984 | Failla et al. . |
| 4,481,952 | 11/1984 | Pawelec . |
| 4,492,232 | 1/1985 | Green . |
| 4,505,414 | 3/1985 | Filipi . |
| 4,509,518 | 4/1985 | McGarry et al. . |
| 4,512,345 | 4/1985 | Green . |
| 4,522,207 | 6/1985 | Klieman et al. . |
| 4,532,925 | 8/1985 | Blake, III . |
| 4,534,351 | 8/1985 | Rothfuss et al. . |
| 4,549,544 | 10/1985 | Favaron . |
| 4,550,715 | 11/1985 | Santangelo et al. . |
| 4,557,263 | 12/1985 | Green . |
| 4,558,706 | 12/1985 | Nakada et al. . |
| 4,562,839 | 1/1986 | Blake, III et al. . |
| 4,572,183 | 2/1986 | Juska . |
| 4,576,166 | 3/1986 | Montgomery et al. . |
| 4,589,421 | 5/1986 | Ullman . |
| 4,598,711 | 7/1986 | Deniega . |
| 4,611,595 | 9/1986 | Klieman et al. . |
| 4,616,650 | 10/1986 | Green et al. . |
| 4,624,254 | 11/1986 | McGarry et al. . |
| 4,633,882 | 1/1987 | Matsuo et al. . |
| 4,646,740 | 3/1987 | Peters et al. . |
| 4,649,904 | 3/1987 | Krauter et al. . |
| 4,662,373 | 5/1987 | Montgomery et al. . |
| 4,662,374 | 5/1987 | Blake, III . |
| 4,674,501 | 6/1987 | Greenburg . |
| 4,674,504 | 6/1987 | Klieman et al. . |
| 4,682,491 | 7/1987 | Pickard . |
| 4,691,853 | 9/1987 | Storace . |
| 4,700,694 | 10/1987 | Shishido . |
| 4,712,549 | 12/1987 | Peters et al. . |
| 4,759,364 | 7/1988 | Boebel . |
| 4,784,137 | 11/1988 | Kulik et al. . |

(List continued on next page.)

U.S. PATENT DOCUMENTS

| | | |
|---|---|---|
| 4,841,888 | 6/1989 | Mills et al. . |
| 4,850,350 | 7/1989 | Jackson . |
| 4,850,355 | 7/1989 | Brooks et al. . |
| 4,858,608 | 8/1989 | McQuilkin . |
| 4,874,364 | 10/1989 | Morris et al. . |
| 4,900,307 | 2/1990 | Kulli . |
| 4,919,152 | 4/1990 | Ger . |
| 4,935,010 | 6/1990 | Cox et al. . |
| 4,944,443 | 7/1990 | Oddsen et al. . |
| 5,026,379 | 6/1991 | Yoon . |
| 5,030,226 | 7/1991 | Green et al. . |
| 5,040,715 | 8/1991 | Green et al. . |
| 5,049,152 | 9/1991 | Simon et al. . |
| 5,084,057 | 1/1992 | Green et al. . |
| 5,100,418 | 3/1992 | Yoon et al. . |
| 5,100,420 | 3/1992 | Green et al. . |
| 5,104,394 | 4/1992 | Knoepfler . |
| 5,104,395 | 4/1992 | Thornton et al. . |
| 5,112,343 | 5/1992 | Thornton . |
| 5,171,247 | 12/1992 | Hughett et al. . |
| 5,171,249 | 12/1992 | Stefanchik et al. . |

OTHER PUBLICATIONS

Information Booklet for Auto Suture ® Skin and Fascia Surgical Stapling Instruments and Disposable Loading Units.

"Information About Dimethyl Silicone Compounds," Dow Corning, 1988.

"Laparoscopic Sterilization with Electrocautery, Spring-Loaded Clips, and Silastic Bands: Technical Problems and Early Complications," Fertility and Sterility, vol. 27, No. 3, Mar. 1976.

"A Clip Applicator for Laparoscopic Sterilization," Fertility and Sterility, vol. 27, No. 9, Sep. 1976.

"Laparoscopic Sterilization with Spring-Loaded Clips: Double-Puncture Technique," The Journal of Reproductive Medicine, vol. 18, No. 5, May 1977.

"Laparoscopic Sterilization with the Spring Clip: Instrumentation development and Current Clinical Experience," American Journal of Obstetrics and Gynecology, vol. 135, No. 8, Dec. 15, 1979.

Karl Storz Endoscopy-America Promotional Advertisement, "It's Your Choice for Tubal Sterilization," 1981.

"An Applicator for the Hulka Fallopian Tube Clip," American Journal of Obstetrics and Gynecology, vol. 139, No. 6, Mar. 15, 1981.

"Metal Clip Techniques Utilizing Pistol Grip Appliers," The American Journal of Surgery, Feb. 1982.

"Results of Experimental Endoscopic Esophagel Varix Ligation," The American Surgeon, Jan. 1988.

Edward Weck & Company Promotional Advertisement, "We've Corrected Everybody's Flaws," Sep. 1986.

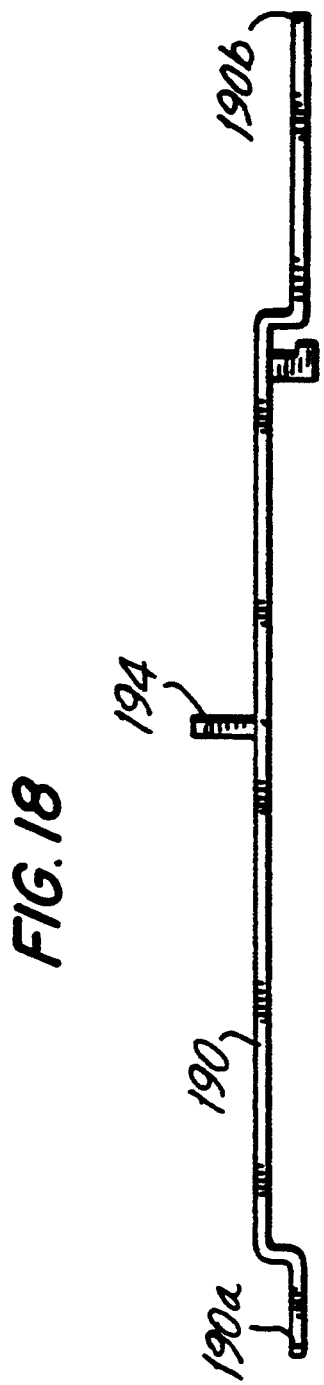

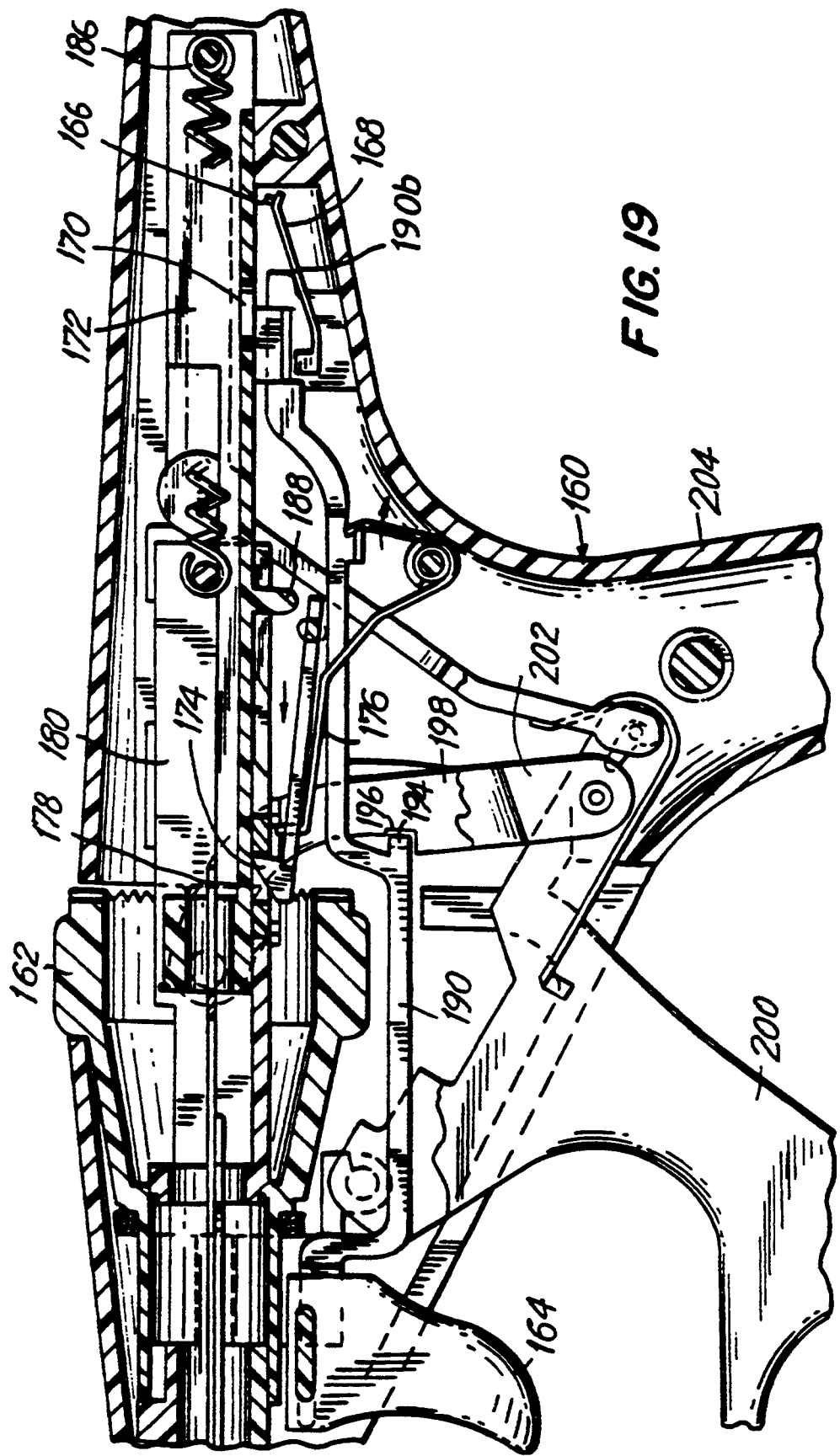

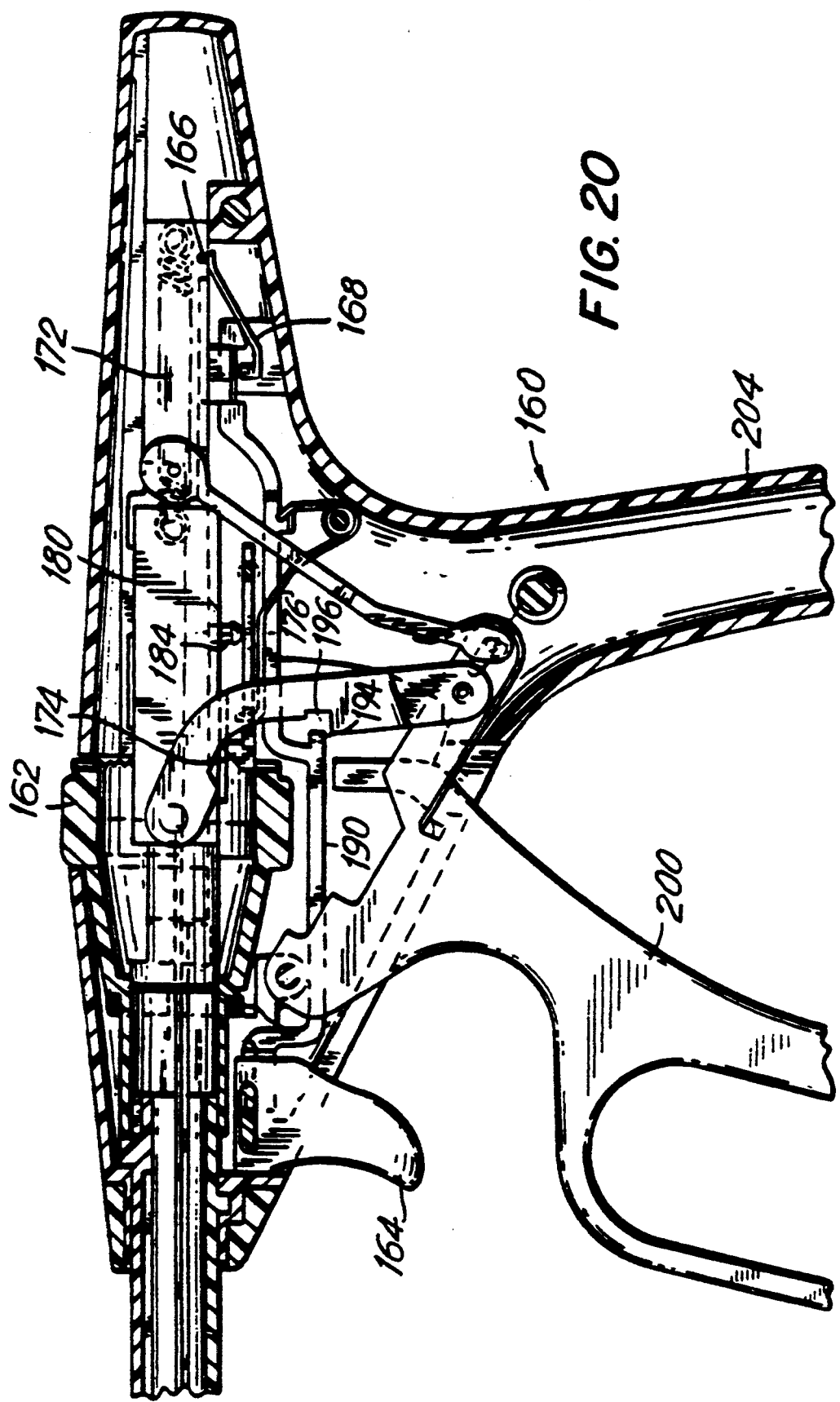

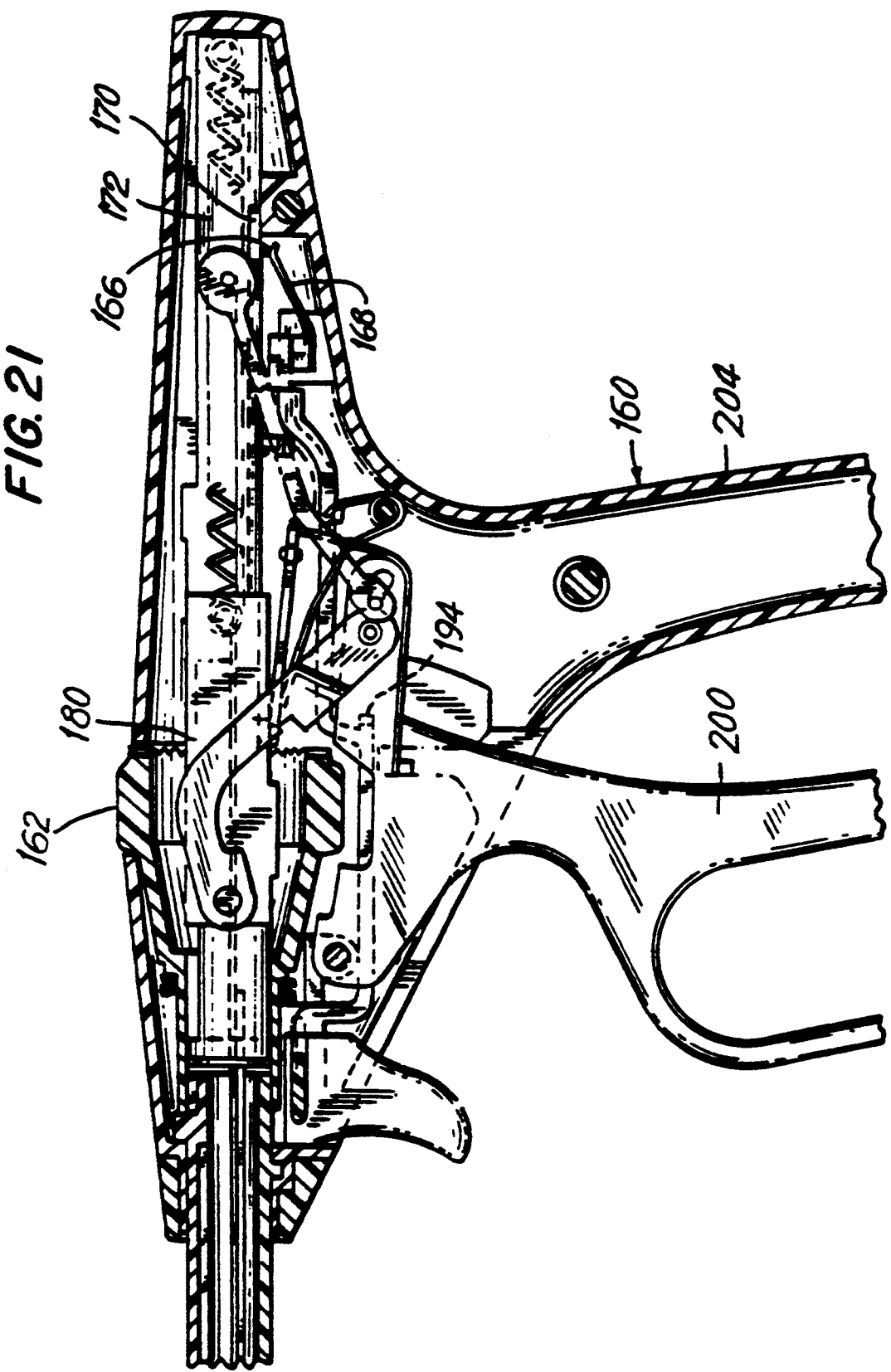

ACTUATING HANDLE FOR SURGICAL INSTRUMENTS

CROSS-REFERENCE TO RELATED APPLICATIONS

This application is a continuation-in-part of application Ser. No. 07/939,029, filed Sep. 2, 1992, now abandoned, which is a continuation of application Ser. No. 07/794,492, filed Nov. 19, 1991, now abandoned, which is a divisional of application Ser. No. 07/530,652, filed May 30, 1990, now U.S. Pat. No. 5,084,057 which is a continuation-in-part of application Ser. No. 07/381,265, filed Jul. 18, 1989, now U.S. Pat. No. 5,100,420.

BACKGROUND OF THE INVENTION

1. Field of the Invention

This invention relates to an apparatus for applying surgical clips, particularly hemostatic clips, to body tissue such as blood vessels. More particularly, this invention relates to a surgical clip applier which prevents simultaneous advancement of surgical clips and actuation of the clip applier, which can be used in laparoscopic or endoscopic procedures.

2. Background of the Related Art

In surgical operations it is often necessary to block blood vessels by applying hemostatic clips. Various types of apparatus for applying such clips to blood vessels are known in the art. See, for example, U.S. Pat. No. 4,616,650, and 4,624,254, both of which are hereby incorporated by reference, which disclose a surgical clip applying apparatus having a pair of ring-like handles. The handles are squeezed to force jaws to move distally relative to the apparatus where they are forced together by a pair of inclined surfaces. A surgical clip between the jaws is thereby squeezed closed. U.S. Pat. Nos. 5,084,057 and 5,100,420 also incorporated herein by reference, are directed to an apparatus and method for applying surgical clips in laparoscopic or endoscopic procedures.

In laparoscopic procedures surgery is performed in the interior of the abdomen through a small incision; in endoscopic procedures surgery is performed in any hollow viscus of the body through narrow endoscopic tubes inserted through small entrance wounds in the skin. Laparoscopic and endoscopic procedures generally require that any instrumentation inserted into the body be sealed, i.e., provisions must be made to ensure that gases do not enter or exit the body through the laparoscopic or endoscopic incision as, for example, in surgical procedures in which the surgical region is insufflated. Moreover, laparoscopic and endoscopic procedures often require the surgeon to act on organs, tissues, and vessels far removed from the incision, thereby requiring that any instruments to be used in such procedures be both long and narrow.

Because endoscopic procedures are more common than laparoscopic procedures, the present invention shall be discussed in terms of endoscopic procedures and apparatus. However, use herein of terms such as "endoscopic", "endoscopically" and "endoscopic portion" among others, refer generally to instruments having elongated and relatively narrow operating portions for insertion into a cannula or endoscopic tube.

SUMMARY OF THE INVENTION

The frame according to the present invention is provided for attachment to an endoscopic section. Surgical clips are stored within the endoscopic section for individual advancement by clip advancing means to a distal position whereby each clip may be deformably applied to body tissue by clip deforming means. The frame includes clip advancing actuating means for actuating the clip advancing means of the endoscopic section, clip deforming actuating means for actuating the clip deforming means of the endoscopic section, and means for preventing actuation of the clip deforming actuating means until the clip advancing actuating means is actuated at least sufficient to advance a clip to the distal position whereby the clip may be deformably applied to body tissue.

The invention also relates to a surgical apparatus adapted to apply surgical clips to blood vessels and the like, in endoscopic or laparoscopic procedures, and generally includes a frame and an endoscopic section. In addition, the surgical apparatus of the present invention provides an interfering device which prevents simultaneous advancement of surgical clips and closure of jaws about the clips so as to reduce the possibility of closing the clip before it is positioned between the jaws or feeding a clip toward the jaws when the jaws are not ready to receive such clip.

The apparatus is provided for endoscopic application of surgical clips to body tissue which includes frame means having endoscopic means connected thereto and extending distally therefrom for storing and individually advancing clips to a distal position thereof, and having means to apply the clip to body tissue and means to prevent actuation of the clip applying means until a clip has been advanced to the distal position.

The apparatus generally comprises a handle section having a frame which is of a size convenient for being held in the palm of the hand and which houses the non-endoscopic body of the apparatus. In an alternate embodiment, the frame is in the form of a pistol grip which may also be conveniently gripped by the surgeon. Other frame configurations, e.g., a scissors grip, are also contemplated. As will be described hereinbelow, the frame houses the above-noted interfering device. An endoscopic section defining a longitudinal axis extends distally from the frame and is rotatable about the longitudinal axis relative to the handle section. The endoscopic section is a long tube-like section having a relatively narrow outer diameter (e.g., about 10 millimeters) for insertion into an endoscopic tube such as a trocar cannula, or a small incision. Other diameters such as 12 millimeters or greater are contemplated. Gaseous seal means is provided, preferably in the endoscopic section, to obstruct passage of gaseous media from the patient's body cavity. Such seal means may be in the form of a sealing block in combination with silicone grease, as disclosed in U.S. Pat. Nos. 5,084,057 and 5,100,420.

The endoscopic section includes a track for holding a longitudinal array of surgical clips, with a spring to bias the clips forwardly in the distal direction. The clips are generally U-shaped pieces of integral construction and comprise two spaced apart legs connected by a bridge portion. The endoscopic section has clip closing means in the form of a pair of flexible opposing jaws which are cammed together into closure positions by a distally-moving channel, and means such as a pusher bar for advancing the surgical clips one at a time to the jaws. A more detailed description of the endoscopic section, and its operation, is provided in Green et al., U.S. Pat. Nos.

5,084,057 and 5,100,420 previously mentioned, both of which are entirely incorporated herein by reference.

The apparatus further has actuating means such as a pivoting handle and connecting links and levers, and a transmission for transferring the pivotal movement of the actuating means linearly along the instrument axis to the endoscopic section of the apparatus. Tubular members are also included with circumferential coupling means such as circumferential notches or projections, which allow a connection of the endoscopic section to the handle section such that linear actuation movement may be transmitted thereto while allowing the endoscopic section to rotate around the instrument axis.

The apparatus further comprises locking means such that once the clip closing jaws have been actuated and opened, the apparatus cannot be reactuated until the locking means is released, usually by a release trigger or button. The locking means comprises a resilient catch (such as a catch in conjunction with a spring) which is movable in response to actuation of the apparatus, i.e., application of a clip, from an unlocked position to a locked position. In the locked position, the locking means is engaged, thereby preventing linear transfer of movement to the clip closing means by the transmission means. Preferably two spring catches are used, one for locking the transmission means for actuating the clip advancing mechanism (e.g., pusher bar), and a second catch for locking the transmission means for actuating the jaw closing mechanism (e.g., the channel). Pressing the release trigger or button releases both the first and second catches. The first catch is released directly thereby allowing the first transmission means to slide forward, and the second catch is released in response to the forward movement of the first transmission means. In addition to releasing the first and second catches, pressing the release trigger or button also actuates the interfering device of the present invention, thereby preventing pivotal movement of the actuating means until the surgical clip is in position between the clip closing jaws.

The surgical clip applier of the present invention, generally, has four basic actions or functions as described hereinbelow.

First, the endoscopic section is introduced into the body and positioned with the jaws engaging the blood vessel to be clipped. This may involve rotation of the endoscopic section relative to the body, either by rotating the apparatus as a whole, or by rotating the endoscopic section relative to the handle section, or by a combination of both actions.

The second action is unlocking the instrument and positioning a clip between the jaws while simultaneously preventing the jaws from closing until the clip is completely positioned between the jaws.

Third, the instrument is adapted to apply a surgical clip to a blood vessel or other tissue. This is accomplished by a camming and clamping action. With a surgical clip in position between the jaws of the instrument and the jaws and clip surrounding a blood vessel, a channel member is moved distally which cams the jaws closed and thereby clamps the surgical clip onto the blood vessel.

The fourth action is that of locking the instrument after a clip has been applied and the jaws opened so that the jaws cannot inadvertently be closed again without further action, e.g., pressing a button to feed a new clip.

After the clipping operation has been completed the instrument may be removed from the body. In one embodiment of the present invention the entire instrument may be discarded. In another embodiment the endoscopic section may be detached and discarded, and the handle section may be retained for a subsequent reuse with a replacement of the endoscopic section.

BRIEF DESCRIPTION OF THE DRAWINGS

FIG. 18 is a view from above of the release lever for the endoscopic clip applier of FIG. 16;

FIG. 19 is a partial cross-sectional view of the handle section of the clip applier of FIG. 16, illustrating the interfering device in engagement with the actuation and transmission system;

FIG. 20 is a partial cross-sectional view of the handle section of the clip applier of FIG. 16, illustrating the pusher drive member extended to its distal-most position and the channel drive member in its proximal-most position; and FIG. 21 is a partial cross-sectional view of the handle section of the clip applier of FIG. 16, illustrating the actuation of the handle after positioning of the surgical clip within the jaws of the endoscopic section.

DETAILED DESCRIPTION OF THE INVENTION

Figure 1:
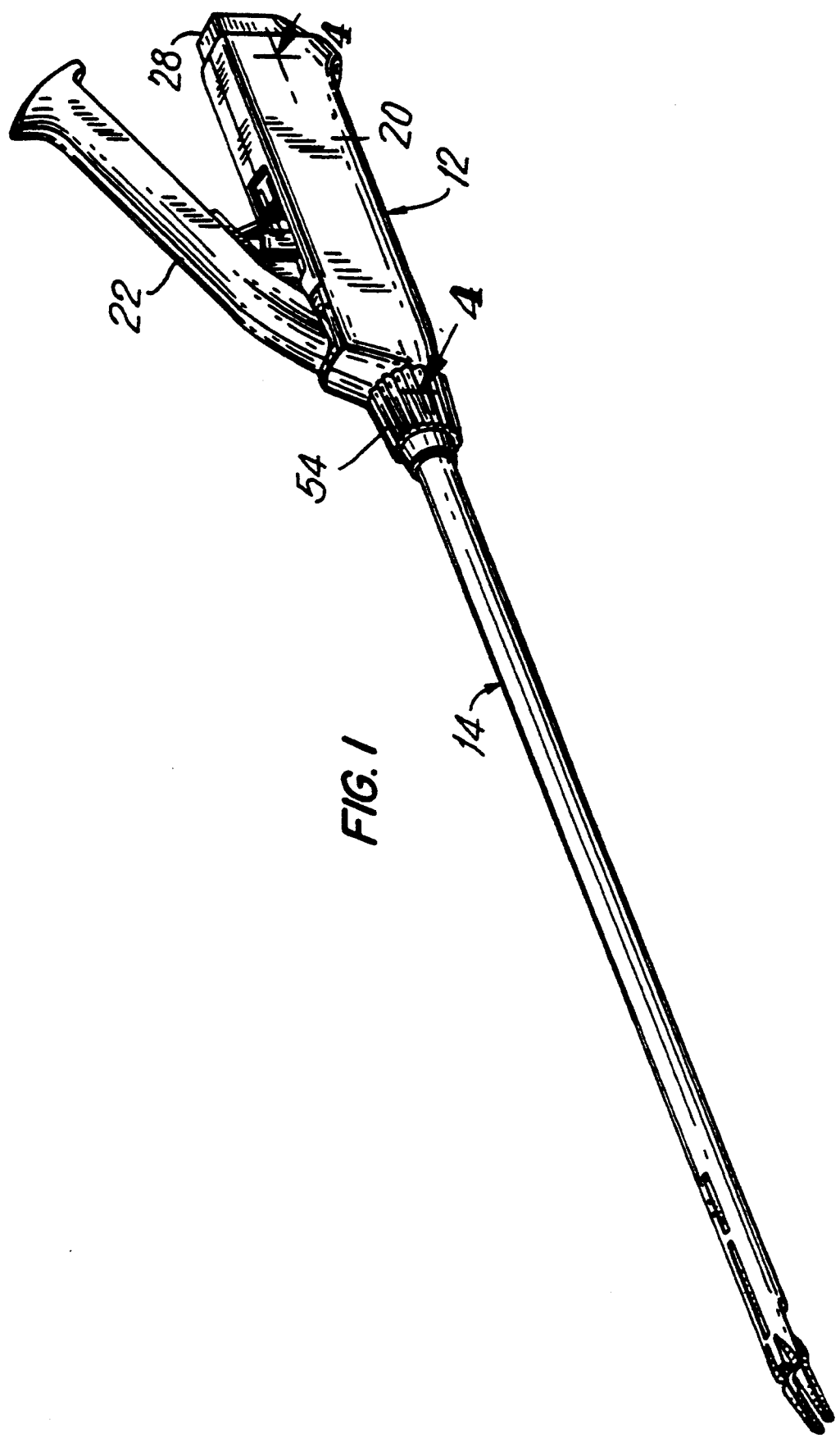
FIG. 1 is a perspective view of an endoscopic clip applier.

Referring to the drawings, and in particular to FIG. 1, the endoscopic clip applier of the present invention, generally indicated by the number 10, generally includes a handle section 12 supporting an endoscopic section 14. The endoscopic section alone may optionally be replaceable and disposable or the entire apparatus may be disposable.

Referring again to FIG. 1, the clip applier 10 is generally configured for applying clips in endoscopic and laparoscopic procedures. The apparatus is preferably constructed as a disposable item of several materials as will be described. Essentially, however, two basic materials are used, i.e., a polycarbonate material such as LEXAN brand plastic material by General Electric Company and stainless steel. Other suitable materials are contemplated.

The endoscopic section 14 includes the same structure and functions in the same manner as the endoscopic section of the apparatus described in parent application Ser. No. 07/794,492, filed Nov. 19, 1991, which is a divisional of application Ser. No. 07/530,652, filed May 30, 1990, now U.S. Pat. No. 5,084,057, which is a continuation-in-part of application Ser. No. 07/381,265, filed Jul. 18, 1989, now U.S. Pat. No. 5,100,420, all of which are incorporated herein by reference.

Figure 2:
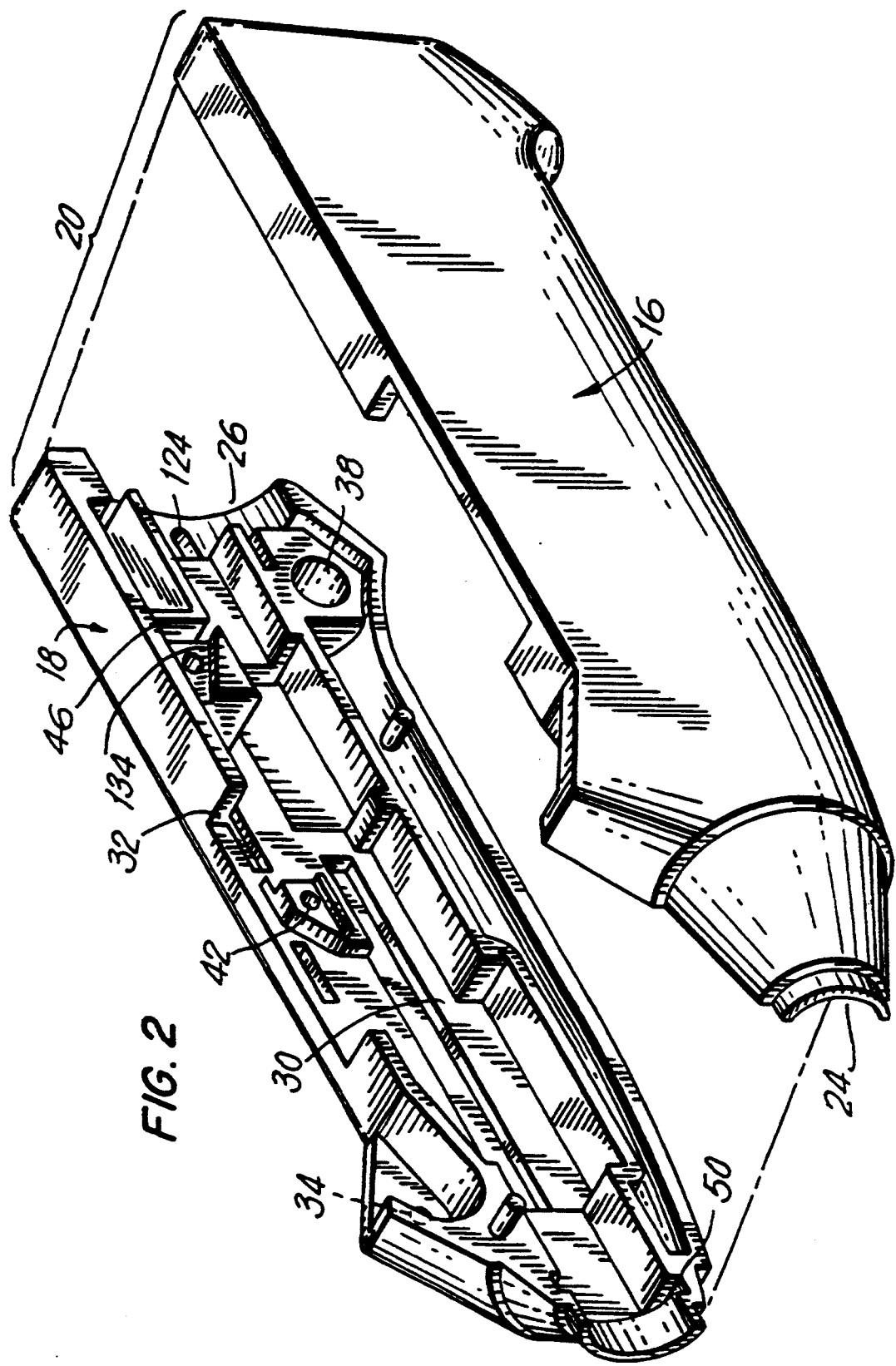
FIG. 2 is a perspective view with parts separated, of the frame of the endoscopic clip applier of FIG. 1, illustrating an interfering guideway for the interfering device of the present invention.
Figure 3:
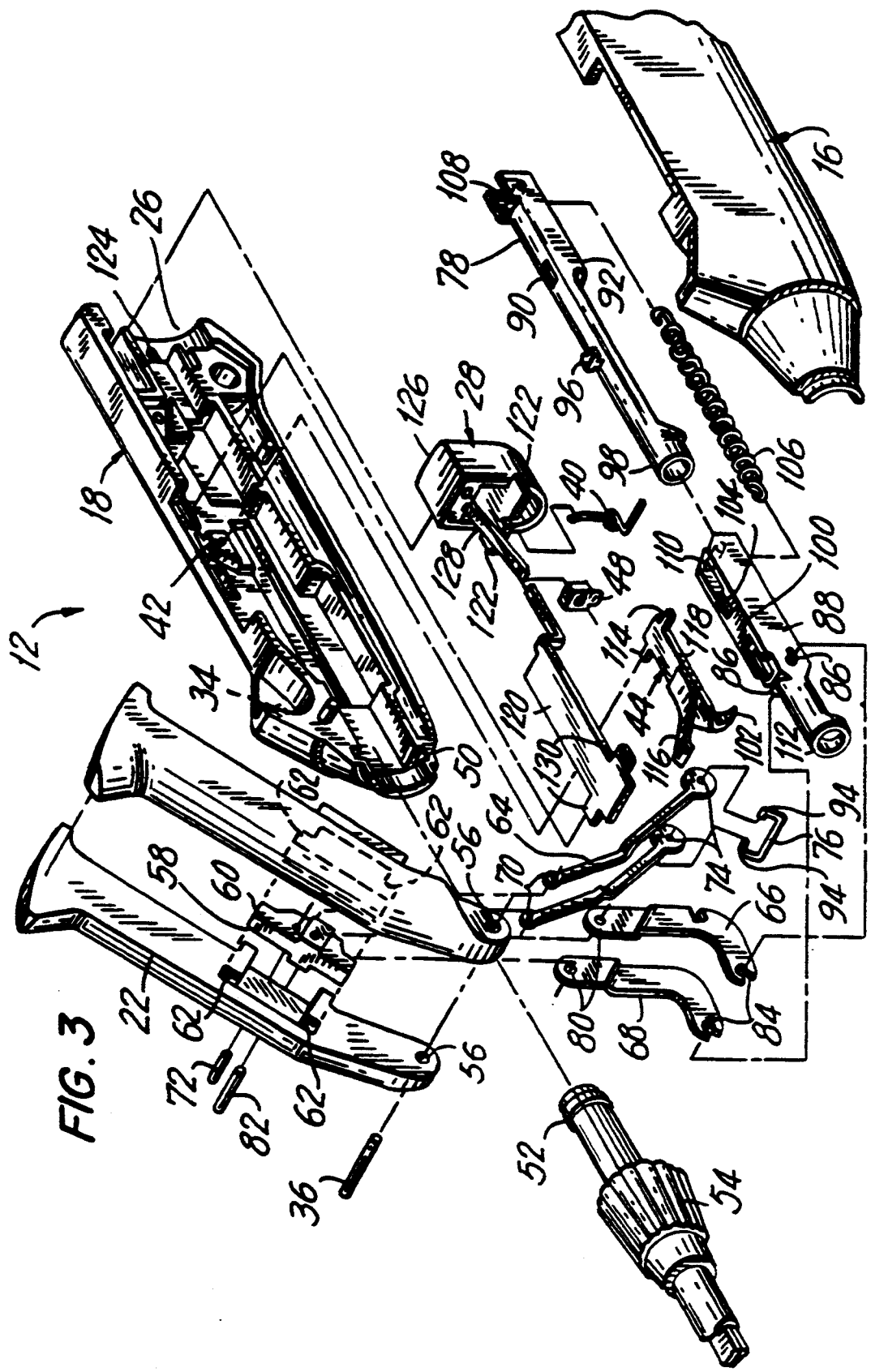
FIG. 3 is a perspective view with parts separated, of the actuating and transmission system of the endoscopic clip applier of FIG. 1, and illustrating the interfering device of the present invention.

Referring now to FIGS. 1, 2 and 3, the apparatus 10 constructed according to the invention is illustrated. Preferably, handle section 12 includes left body portion 16 and right body portion 18 which define hand grip 20 of handle section 12. These body portions may be either cast, molded or machined pieces of polymeric resin or metal. The left and right portions are substantially identical, although mirror images of each other, and may optionally be fastened together by means of fastening screws, rivets, welds, adhesives, or other means of joining the body portions may be used. Handle 22 is pivotally secured to hand grip 20 and is provided to actuate transmission mechanisms positioned within hand grip 20, as will be discussed below.

Hand grip 20 is somewhat elongated, as shown in FIG. 2, and is of overall size and shape convenient for being held in the palm of the hand. Further, hand grip 20 has an interior surface which defines a distal opening 124 for receiving a portion of endoscopic section 14, a proximal opening 26 for receiving release button 28 and interior 5 transmission guideway 30 which allows movement of the transmission mechanisms therewithin. Hand grip 20 also includes interior guideway 32 for slidably maintaining the interfering device of the present invention therewithin, aperture 34 for reception of pin 36 (shown in FIG. 3) which pivotally secures handle 22 to hand grip 20. Backstop notch 38 is provided to receive a portion of spring 40, and mounting notch 42 is provided to maintain spring 44 within hand grip 20. Channel 46 is provided for slidable reception of catch 48 which is slidably secured to release button 28 so as to allow catch 48 to slide into and out of engagement with the first transmission mechanism, best shown in FIG. 3. Annular channel 50 is provided to receive a circumferential tab 52, shown in FIG. 3, secured adjacent the proximal end of endoscopic section 14. Annular channel 50 is configured and dimensioned to receive the proximal end portion of endoscopic section 14 in a manner to facilitate rotation of endoscopic section 14 with respect to handle section 12 via hand operable wheel 54. This channel is also adapted to retain endoscopic section 14 while preventing longitudinal movement of the endoscopic section with respect thereto.

Referring further to FIGS. 2 and 3, handle 22 is an elongated piece which is pivotally mounted to the distal end of hand grip 20 by pin 36 which is disposed through aperture 56 in handle 22 and aperture 34 in hand grip 20. Handle 22 may be of monolithic construction or may be separate pieces fastened together by means of welds, adhesives or the like. Aperture 58 of handle 22 is adapted to receive securing block 60 which is secured to handle 22 by engaging notches 62. In addition, aperture 58 provides spacing for pivotal movement of pusher links 64 and channel links 66 and 68 which are pivotally secured to securing block 60.

Referring again to FIG. 3, pusher links 64 are irregularly shaped members as shown, resembling somewhat a pair of elongated curved pieces having upper apertures 70 for reception of pin 72 which pivotally secures the pusher links to securing block 60, and lower apertures 74 for pivotally securing crossbar 76 therebetween. In this configuration, the curvature of pusher links 64 enhances the camming action of the first embodiment of the interfering device of the present invention, as will be discussed below. As shown, pusher links 64 provide means for transferring pivotal movement from handle 22 to linear movement of pusher drive member 78.

As shown in FIG. 3, channel links 66 and 68 are curved elongated pieces having upper apertures 80 for receiving pin 82 which pivotally secures the channel links to securing block 60, and lower apertures 84 for engaging protrusions 86 of channel drive member 88 so as to pivotally secure channel links 66 and 68 to channel drive member 88. Channel links 66 and 68 are provided to transfer and convert pivotal movement from handle 22 to linear movement of channel drive member 88, and to act as a load limiter as well.

Continuing to refer to FIG. 3, pusher drive member 78 is part of a first transmission mechanism for transmitting linear movement to the pusher bar of the endoscopic section. Preferably, pusher drive member 78 is in the form of an elongated structure having a tubular portion at its distal end and a channel-like configuration as the proximal end and is slidably positioned within transmission guideway 30 of hand grip 20, shown in FIG. 2. Pusher drive member 78 also includes aperture 90 for reception of catch 48 of release button 28. Channel 92 within pusher drive member 78 is provided to engage ends 94 of crossbar 76 to facilitate distal movement of pusher drive member 78, while camming pin 96 is provided to engage spring clip 44 upon actuation of release button 28. Tubular portion 98 at the distal end of the pusher drive member 78 is provided to engage the proximal end of the pusher bar of endoscopic section 14.

Referring again to FIG. 3, channel drive member 88 is part of a second transmission mechanism for transmitting linear movement to a corresponding channel of the endoscopic section. Preferably, channel drive member 88 is in the form of an elongated structure having a tubular portion at its distal end and a channel-like configuration as the proximal end and is slidably positioned within transmission guideway 30 of hand grip 20, shown in FIG. 2. Channel drive member 88 also includes aperture 100 for engaging catch 102 of spring clip 44, and proximal slot 104 for receiving camming pin 96 when the first transmission mechanism is actuated. Pusher drive member 78 is positioned for slidable movement within channel drive member 88 and the two drive members are biased into alignment by mainspring 106 axially disposed within pusher drive member 78 and which is attached at its proximal end to pin 108 of pusher drive member 78 and at its distal end to pin 110 of channel drive member 88. Tubular portion 112 of channel drive member 88 is provided for engaging the proximal end of the corresponding channel of the endoscopic section.

As shown in FIG. 3, leaf spring or spring clip 44 is a catch device used to lock channel drive member 88 in the distal position after the apparatus has been actuated. Spring clip 44 has a proximal end with tabs 114, as shown, for mounting in notch 42 of hand grip 20. At its distal end, resilient spring clip 44 has catch 102 which is engageable with aperture 100 of the channel drive member 88 in response to resilient arm 116. Spring clip 44 also includes camming surface 118 which is contacted by camming pin 96 when pusher drive member 78 moves in the distal direction, thereby depressing spring clip 44 and disengaging and unlocking channel drive member 88.

Figure 4:
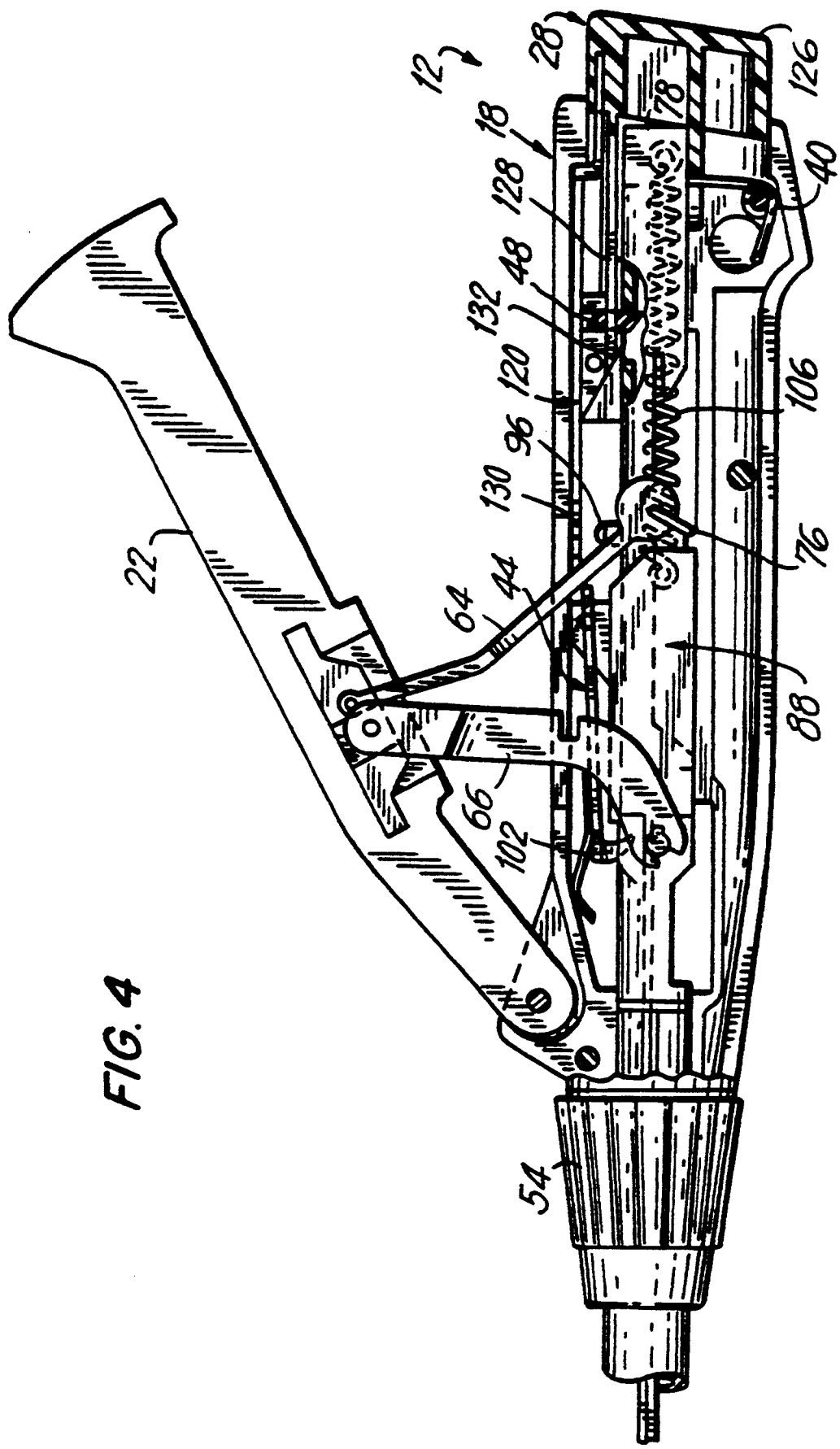
FIG. 4 is a partial cross-sectional view of the handle section of the endoscopic clip applier of FIG. 1 taken along line 4—4 of FIG. 1 and illustrating the actuating and transmission system prior to loading a clip.

Referring now to FIG. 3 in conjunction with FIG. 4, release button 28 and related interfering device 120 are shown. Release button 28 is configured to be positioned within proximal opening 26 of hand grip 20 between and by means of limiting tabs 122 which engage slots 124 of hand grip 20 and biasing spring 40. Limiting tabs 122 limit the proximal movement of the release button by engaging the proximal end of slots 124, while biasing spring 40 normally provides a force to bias release button 28 in the proximal direction. Release button 28 has a proximal end 126 which projects through aperture 26 in hand grip 20. Catch 48 of release button 28 is slidably positioned at a distal end of resilient arm 128, and is adapted for reception in aperture 90 of pusher drive member 78 to lock the clip advancing system in the ready position, i.e., the pusher bar is positioned just proximal of the next clip in the endoscopic section. Interfering device 120 has a proximal end secured to release button 28 and extends distally therefrom. Interfering device 120 also includes tabs 130 positioned adjacent the distal end thereof, which engage corresponding interior guideways 32 located within hand grip 20, shown in FIG. 2. The operation of different embodiments of interfering device 120 will be described below.

As noted previously, according to the present invention, gaseous seal means is preferably provided in the endoscopic section of the instrument to obstruct the passage of the insufflating gaseous media from the patient's body cavity. As described above, such seal means may be in the form of a sealing block, or it may be in the form of silicone grease in combination with such sealing block. The gaseous seal means may be in association either with the endoscopic section or the handle section, or both. Preferably, the seal means is positioned within the endoscopic section.

The operation of the first embodiment of the interfering device of the present invention within the palm grip handle section will be described with reference to FIGS. 4–9. Initially, the endoscopic clip applier is provided in the locked position, i.e., there is no clip loaded between the jaws of the endoscopic section. At this point, the jaws are biased open and are free to cam between the open and closed positions. This facilitates insertion of the endoscopic section into an endoscopic tube or into the body since the jaws can cam partially closed, thereby avoiding interference with the positioning of the instrument. In this condition distal movement of pusher drive member 78 is prevented by engagement of slidable catch 48 of release button 28 with aperture 90 of pusher drive member 78. As a result, squeezing of handle 22 is prevented by the engagement of catch 102 of spring clip 44 with aperture 100 of channel drive member 88, as noted above.

Figure 5:
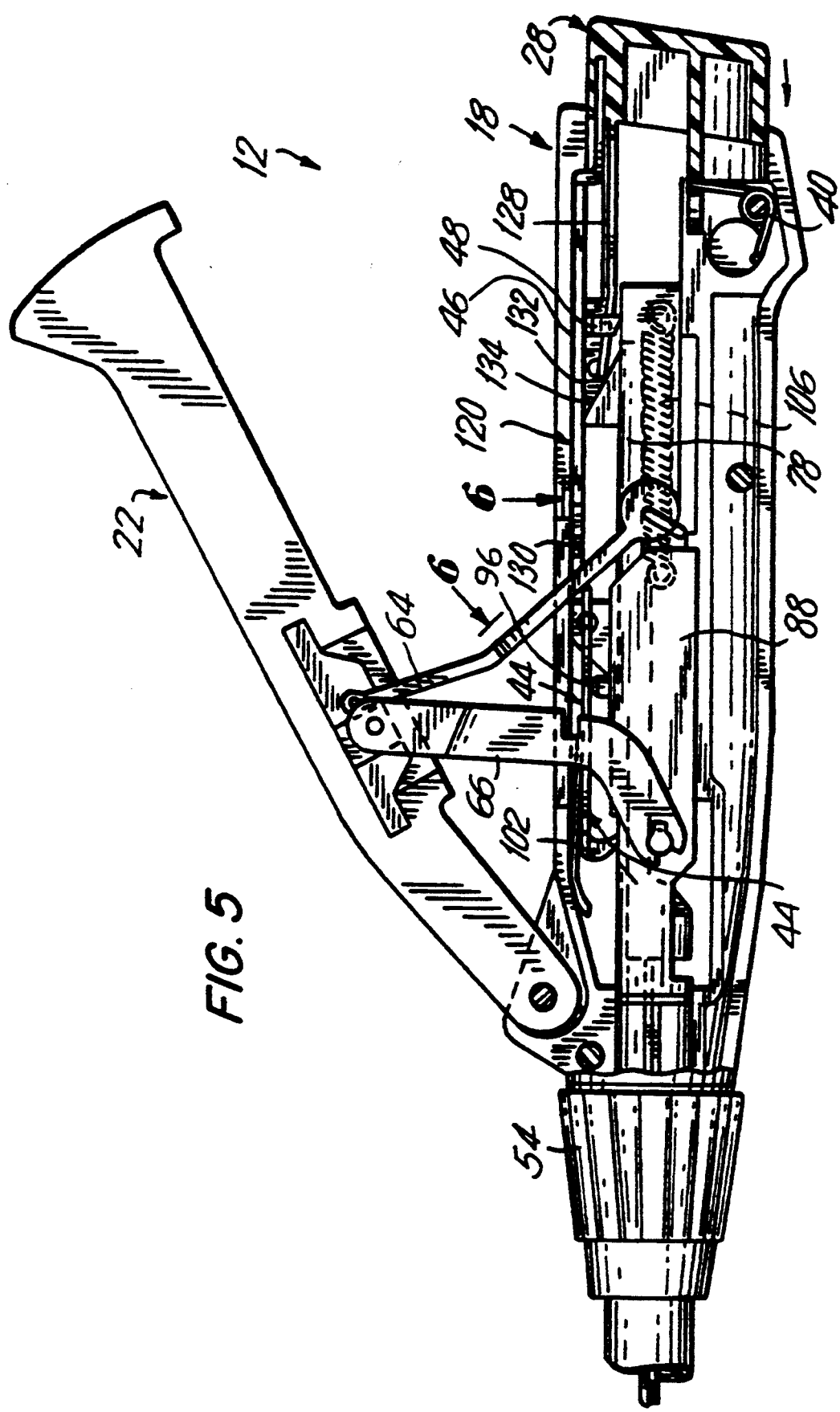
FIG. 5 is a partial cross-sectional view similar to FIG. 4, illustrating the handle section in the ready-to-fire position.

Referring now to FIGS. 4 and 5, when the endoscopic section of the clip applier has been properly positioned within a body cavity or other appropriate location, the user releases the first and second transmission means from the locked position by pressing release button 28. This movement causes bevelled tip 132 of resilient arm 128 to slide along ramps 134 in hand grip 20, thus releasing catch 48 from aperture 90 in pusher drive member 78 and disengaging the first transmission means, i.e., pusher drive member 78. Upon release, pusher drive member 78 slides forward to provide advancement of the clip next-in-line, while also releasing catch 102 of spring clip 44 from aperture 100 of channel drive member 88, i.e., the second transmission means, as explained above. Through pusher drive member 78, the first transmission mechanism transfers motion to the pusher bar of the endoscopic section which has a distal pusher end located proximal of the distal-most clip in the array. When the pusher bar moves forward, the distal-most clip is advanced into the jaws of the endoscopic section. Channel drive member 88, upon being released, is now free to move distally upon squeezing of handle 22 thus moving the channel distally within the endoscopic section.

Figure 6:
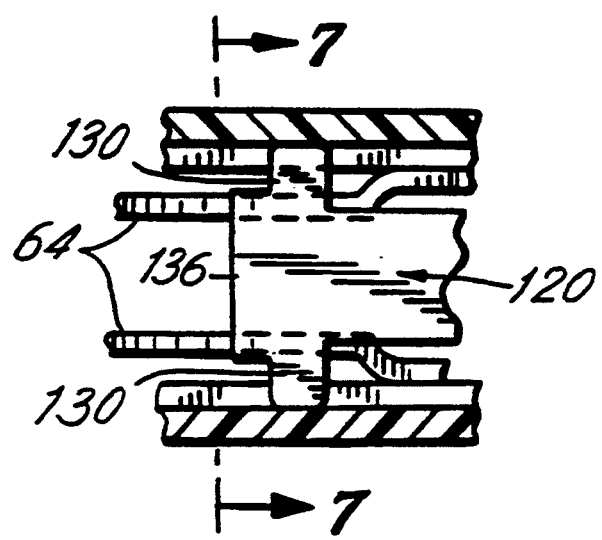
FIG. 6 is a sectional view of the interfering device of the present invention taken along line 6—6 of FIG. 5.
Figure 7:
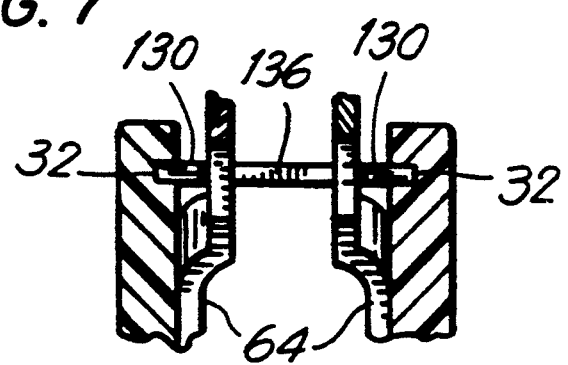
FIG. 7 is a sectional view of the interfering device of the present invention taken along line 7—7 of FIG. 6.
Figure 8:
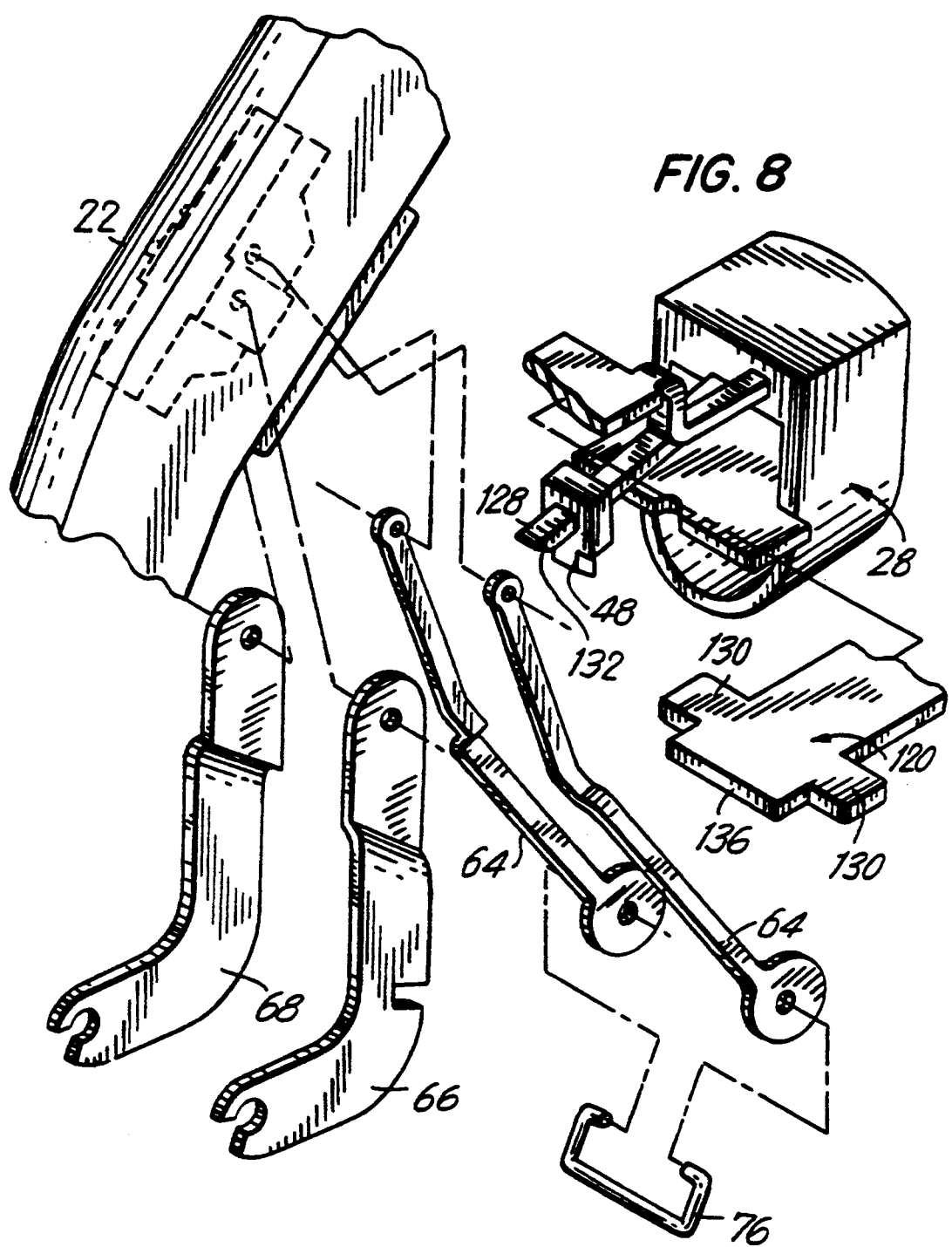
FIG. 8 is an enlarged sectional view with parts separated of the operative linkages of the endoscopic clip applier of FIG. 1, illustrating the orientation of the distal end of the interfering device of the present invention.

The structure and function of release button 28 and the related interfering system will now be described with reference to FIGS. 5–8. In addition to releasing the first and second transmission mechanisms, as explained above, the release button according to the present invention also advances interfering device 120 in the distal direction. Distal movement of release button 28 thus causes tabs 130 of interfering device 120 to slide within interior guideways 32 of hand grip 20 to an interfering position. The interfering position is the position where engaging surface 136 of interfering device 120 engages pusher links 64 to prevent subsequent proximal movement of pusher links 64, as shown in FIGS. 6–8. As a result, if actuation of handle 22 is attempted prior to final positioning of the surgical clip within the jaws of endoscopic section 14, engaging surface 136 will prevent motion of pusher links 64 for a period of time sufficient to allow the surgical clip to be completely positioned within the jaws of endoscopic section 14. When the clip is positioned between the jaws of endoscopic section 14, actuation of the first transmission mechanism releases the second transmission mechanism. Once the clip is positioned between the jaws, the instrument is ready to be actuated for clip application.

Figure 9:
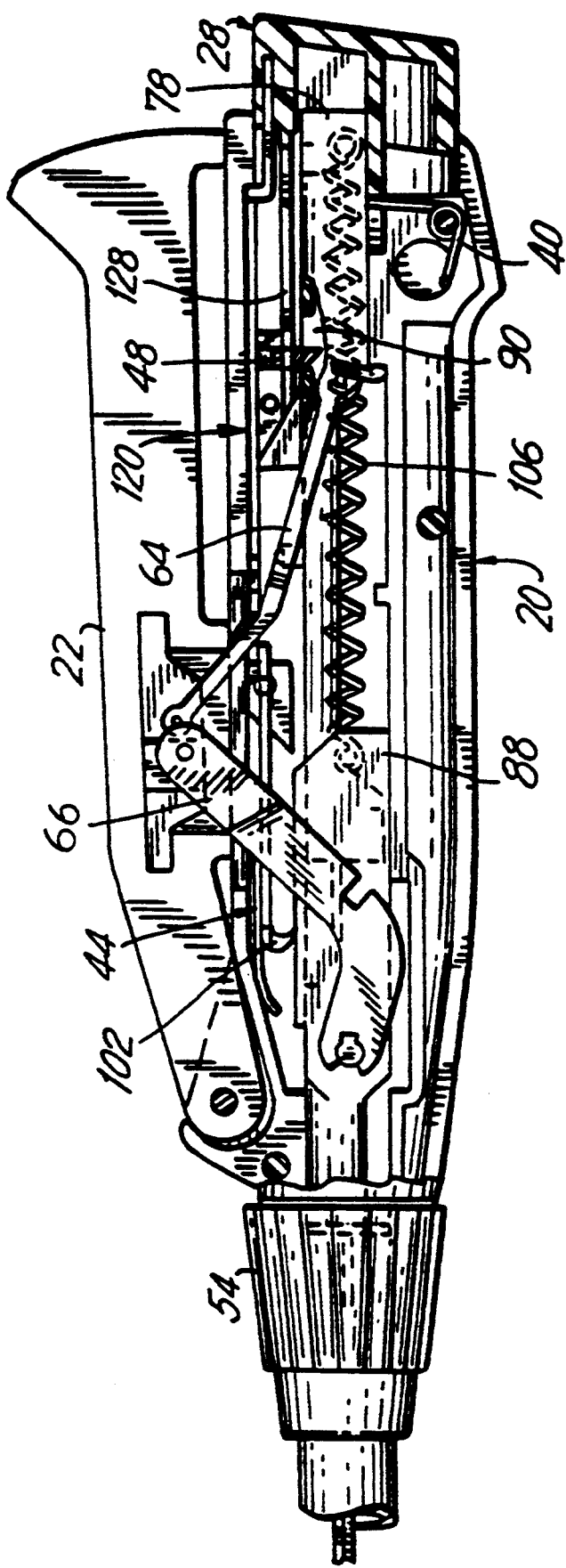
FIG. 9 is a partial cross-sectional view similar to FIG. 4, illustrating the handle in the fired position.

After release button 28 returns to its normal position, the endoscopic clip applier may be actuated by manually gripping and pivoting handle 22 toward hand grip 20, as shown in FIG. 9. When handle 22 is advanced toward hand grip 20, pusher links 64 move pusher drive member 78 proximally to the rear of the instrument, thereby repositioning the pusher bar of the endoscopic section behind the next-in-line clip. In addition, channel links 66 and 68 simultaneously advance channel drive member 88 distally, thereby causing the jaws of the endoscopic section to be closed. This is accomplished when the distally moving channel drive member 88 pushes its corresponding channel in endoscopic section 14 distally, thereby camming the jaw blade into the closed position for applying the surgical clip to tissue. Pusher drive member 78 is then locked in the proximal position when catch 48 of release button 28 engages aperture 90 in pusher drive member 78, as noted above. Channel drive member 88 is then locked in the proximal position when catch 102 of spring clip 44 engages aperture 100 of channel drive member 88 upon return of handle 22 and channel drive member 88 to their normal position. As will be appreciated, the apparatus remains locked until the release button 28 is pressed, thereby unlocking the instrument as explained above.

Figure 10:
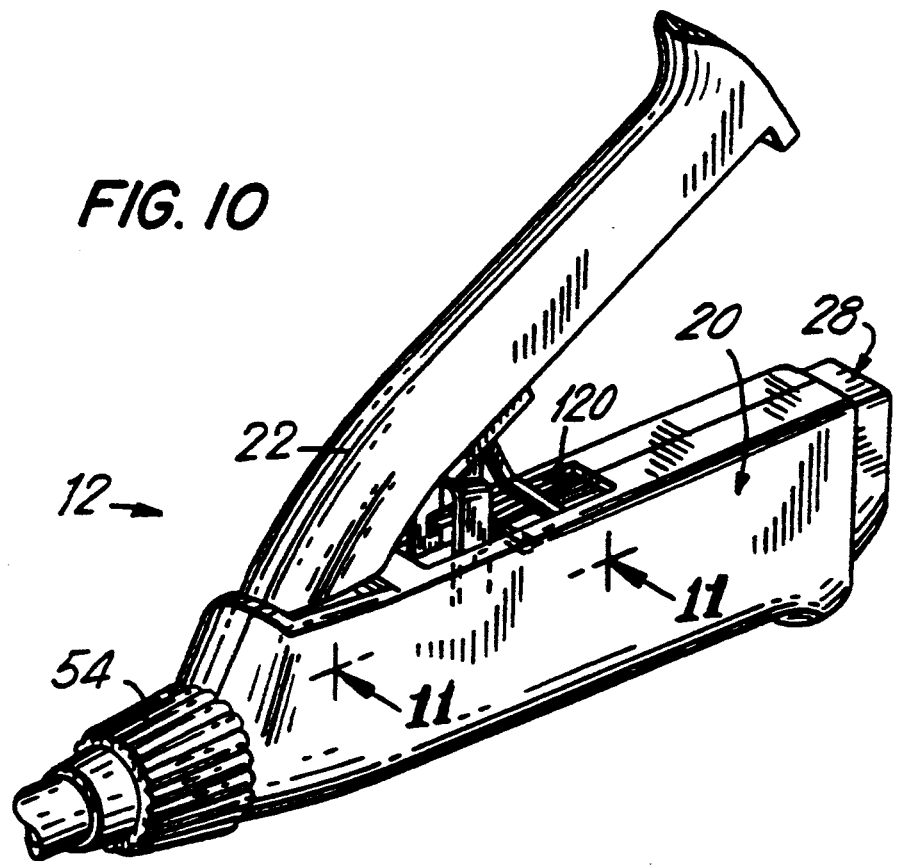
FIG. 10 is a perspective view of the handle section of an endoscopic clip applier according to the invention, illustrating an alternative embodiment of the interfering device of the present invention.
Figure 11:
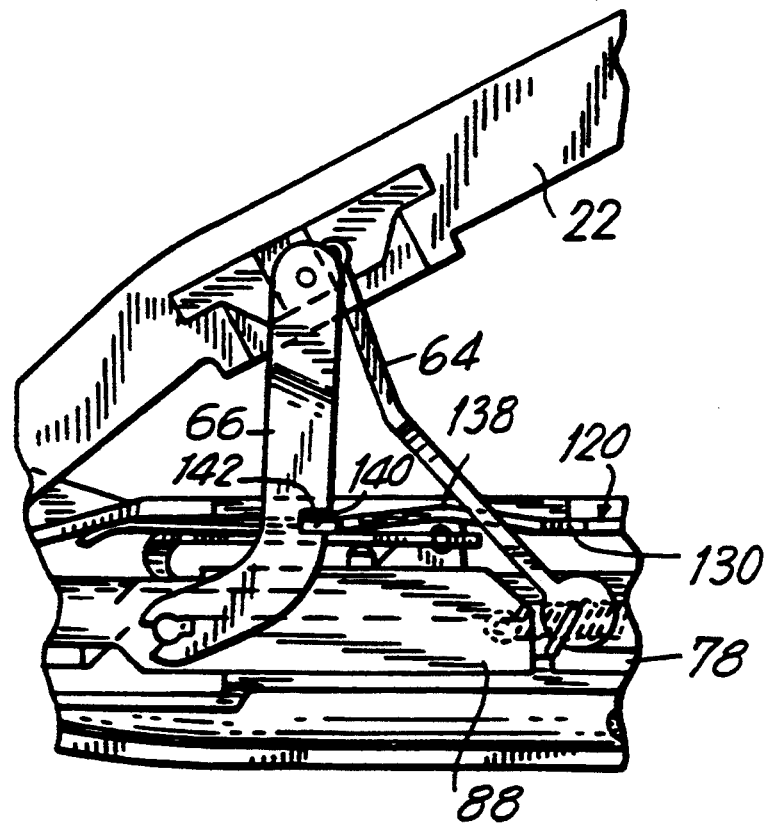
FIG. 11 is a partial view taken along line 11—11 of FIG. 10, illustrating the respective orientation of the interfering device with the channel link when the pusher release button is activated.
Figure 12:
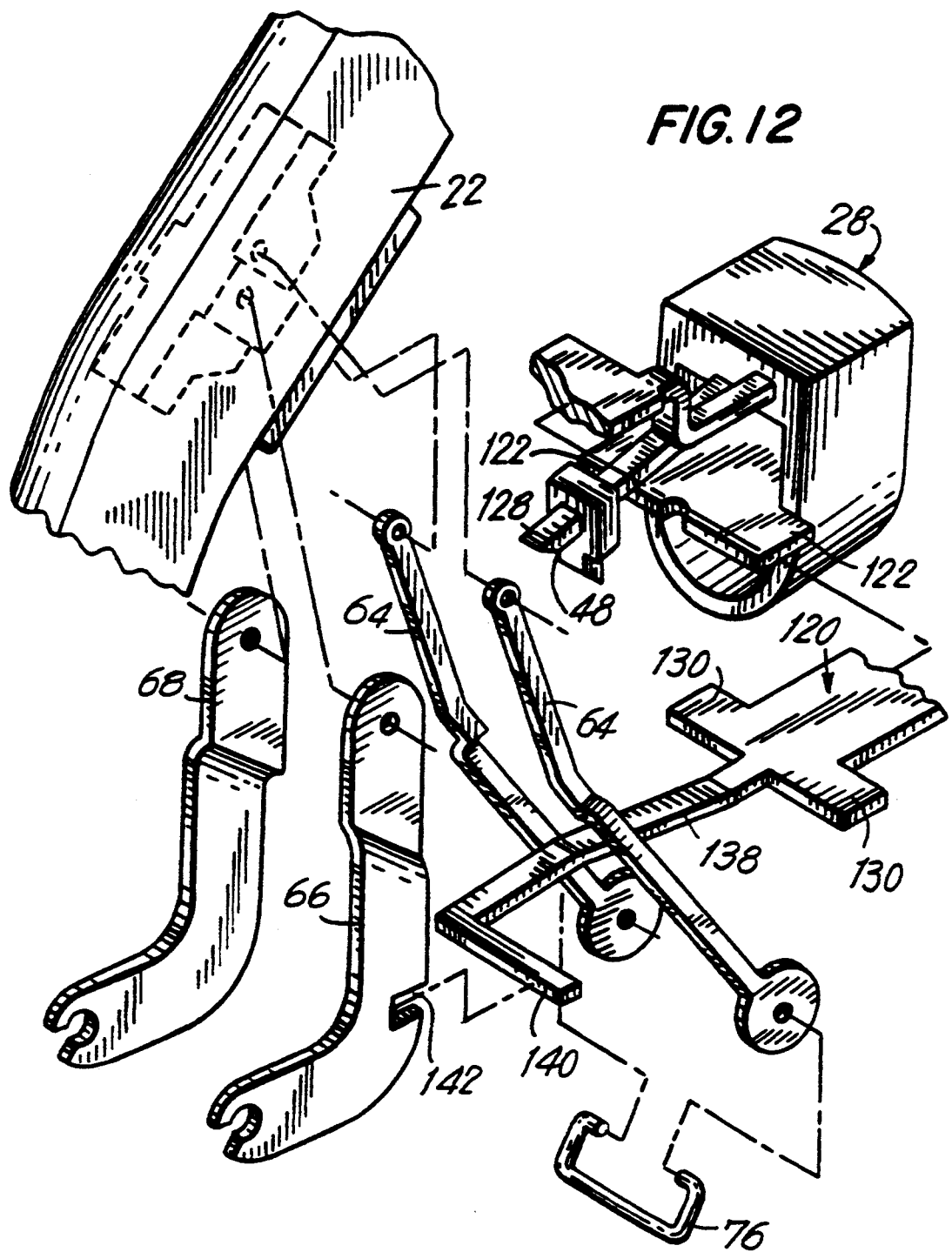
FIG. 12 is an enlarged perspective view with parts separated of the operative linkages between a portion of the handle and the frame of FIG. 10, illustrating the orientation of the distal end of the interfering device of the present invention.

Referring now to FIGS. 10-12, a second embodiment of the interfering device of the present invention within the palm grip handle section will now be described. As shown in FIGS. 11 and 12, the second embodiment for the interfering device is structurally similar to the first embodiment. However, in this embodiment arm 138 extends longitudinally from the distal end of interfering device 120 and has transverse arm 140 at the distal end thereof, as shown.

In operation, distal movement of finger operable release button 28 causes tabs 130 of interfering device 120 to slide within interior guideways 32 of hand grip 20 to an interfering position, as noted above. Preferably, the interfering position for the second embodiment of interfering device 120, is the position where arm 140 engages slot 142 of channel link 66 to prevent subsequent movement of channel links 66 and 68, as shown in FIG. 11. As a result, if actuation of handle 22 is attempted prior to final positioning of the surgical clip within the jaws of endoscopic section 14, arm 140 in combination with arm 138 will prevent motion of channel links 66 and 68 for a period of time sufficient to allow the surgical clip to be completely positioned within the jaws of endoscopic section 14. As noted above, when the clip is positioned between the jaws of endoscopic section 14, the actuation of the first transmission mechanism releases the second transmission mechanism. Once the clip is positioned between the jaws, the instrument is ready to be actuated for clip application, as noted above.

Figure 13:
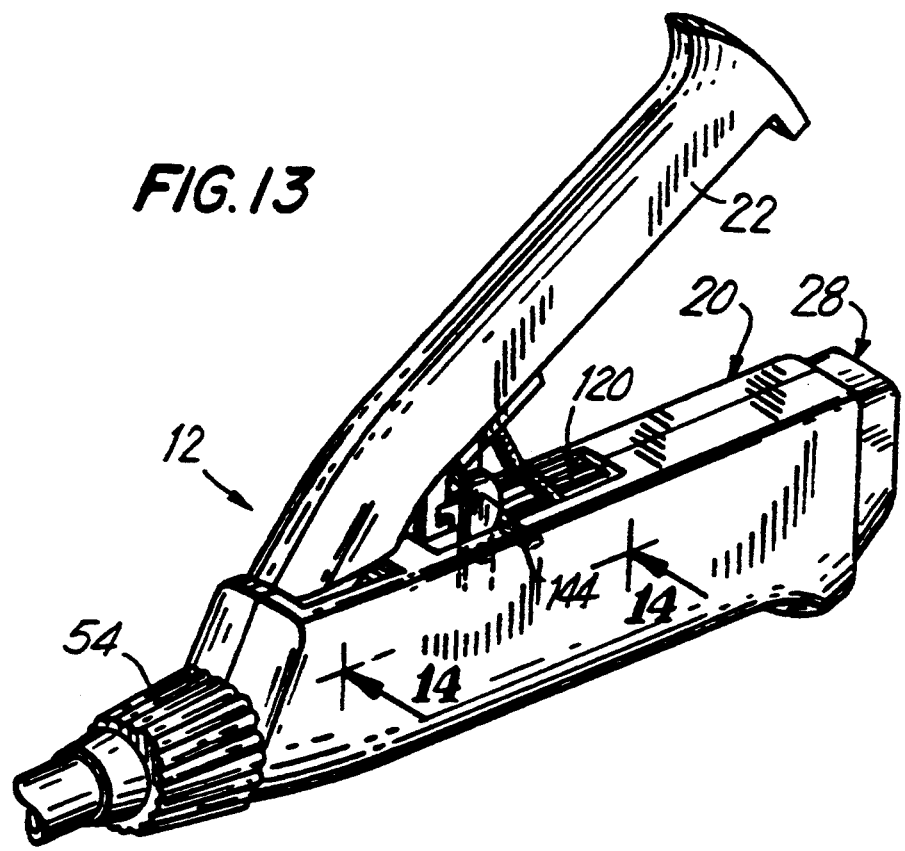
FIG. 13 is a perspective view similar to FIG. 10 of another alternative embodiment of the invention, illustrating a channel link having a lobe formed thereon.
Figure 14:
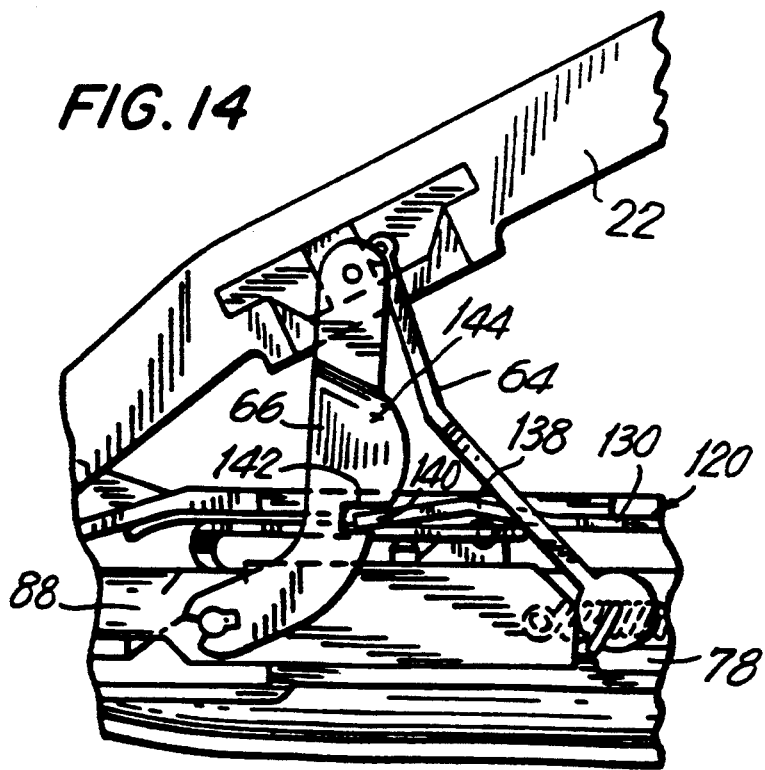
FIG. 14 is a view taken along line 14—14 of FIG. 13, illustrating the respective relative orientation of the lobed channel link and the interfering device of the invention.
Figure 15:
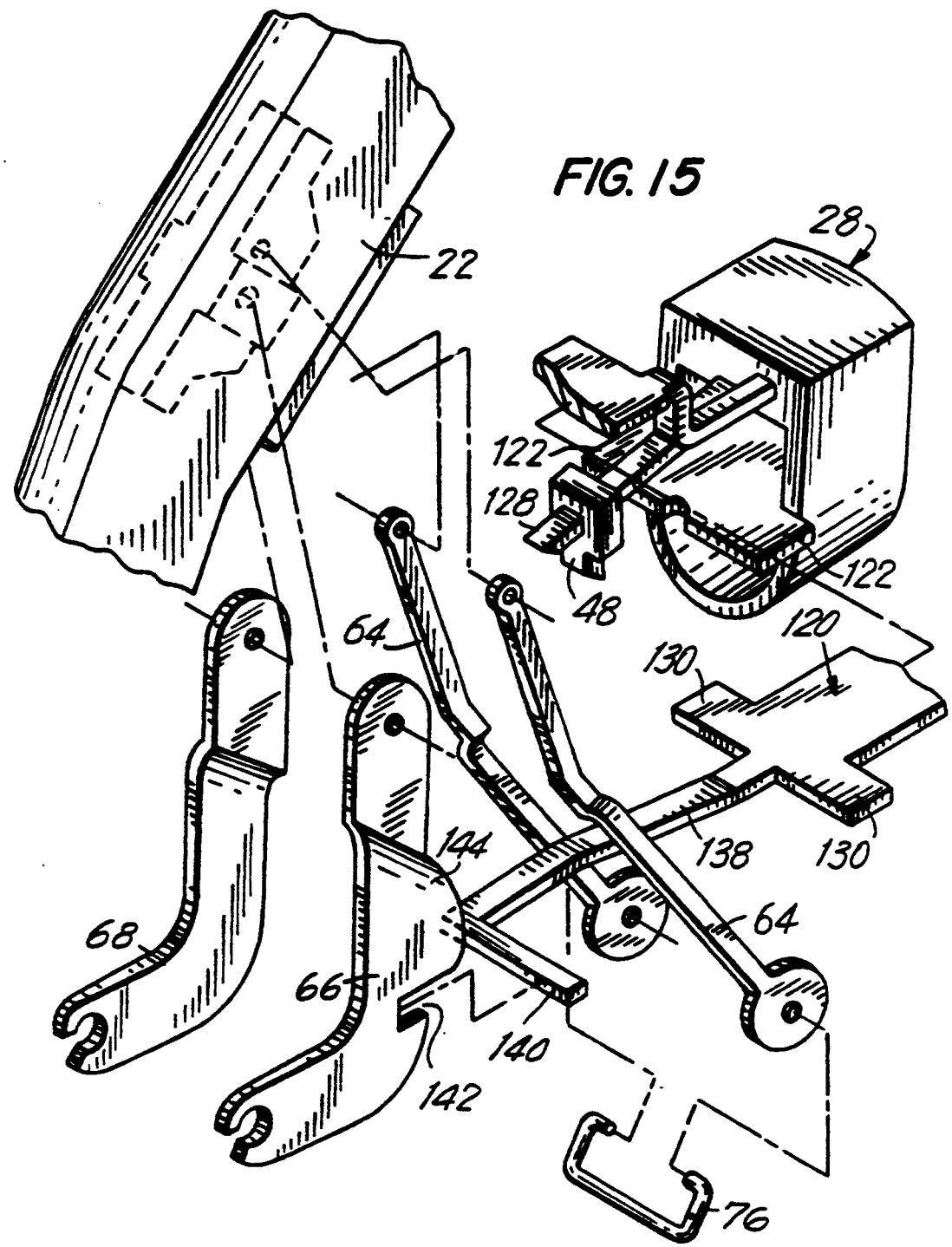
FIG. 15 is an enlarged perspective view with parts separated of the operative linkages between a portion of the handle and the frame of FIG. 13, illustrating the respective orientation of the distal end of the interfering device.

Referring now to FIGS. 13-15, the palm grip handle section 12 may also include lobe 144 positioned adjacent to slot 142 on channel link 66 as shown. Preferably, lobe 144 is a protrusion formed on channel link 66 and extends towards the rear of handle section 12, i.e., proximally. Lobe 144 is provided to prevent distal movement of release button 28, i.e., actuation of the first transmission mechanism, until the jaws of endoscopic section 100a have completely opened. As a result, lobe 144 prevents loading of a clip between the jaws of endoscopic section 14 until the jaws are ready to receive the next clip in the clip array and prevents deformation of the clip and/or disabling the clip applier.

It should be noted that the above-described interfering devices for the palm grip handle section represent preferred embodiments for preventing simultaneous advancement of clips into the jaws and closing of the jaws in the event the operator inadvertently actuates both systems simultaneously.

Figure 16:
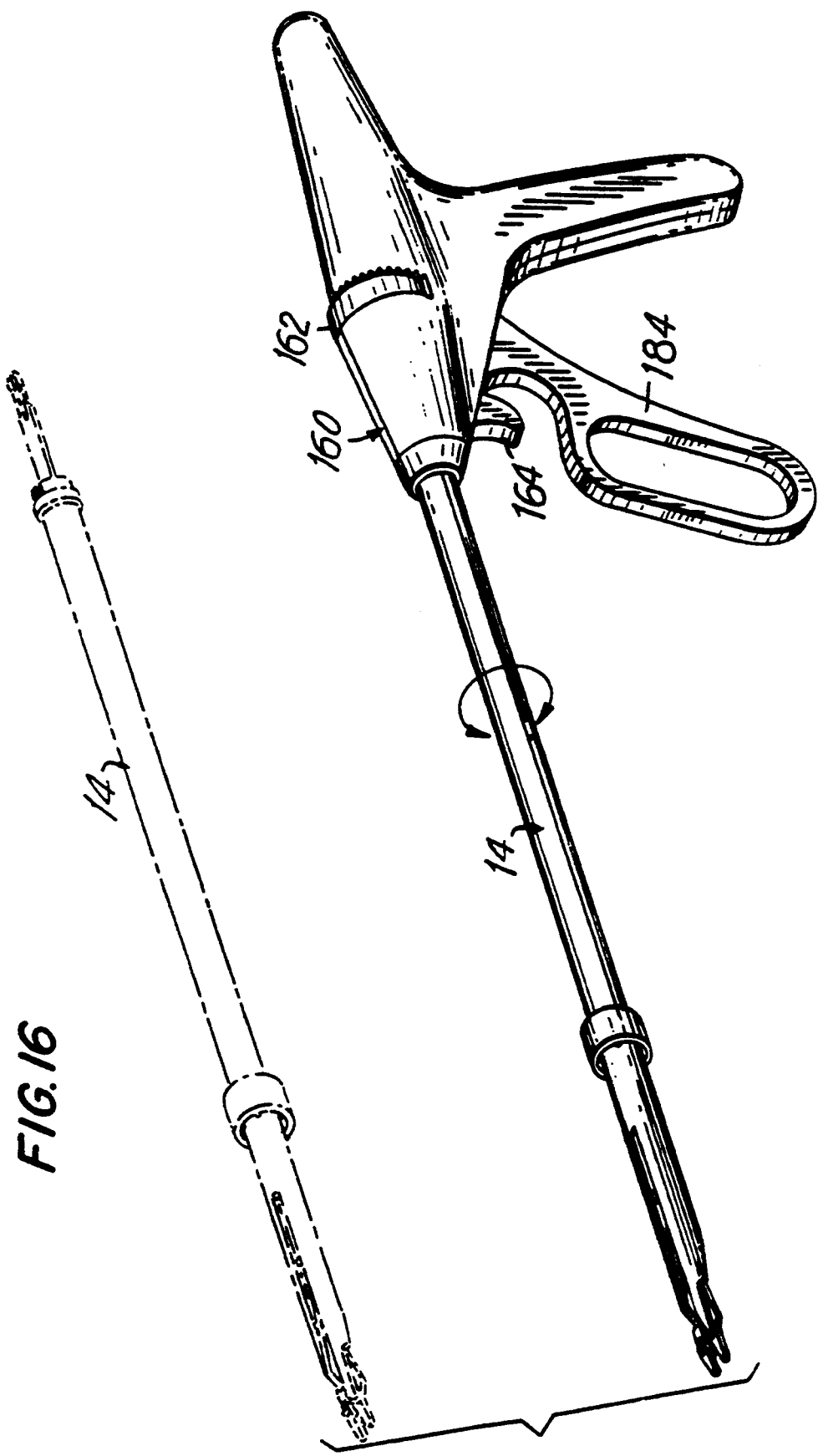
FIG. 16 is a perspective view of another alternative embodiment of an endoscopic clip applier of the invention, incorporating a handle section having a pistol grip configuration.
Figure 17:
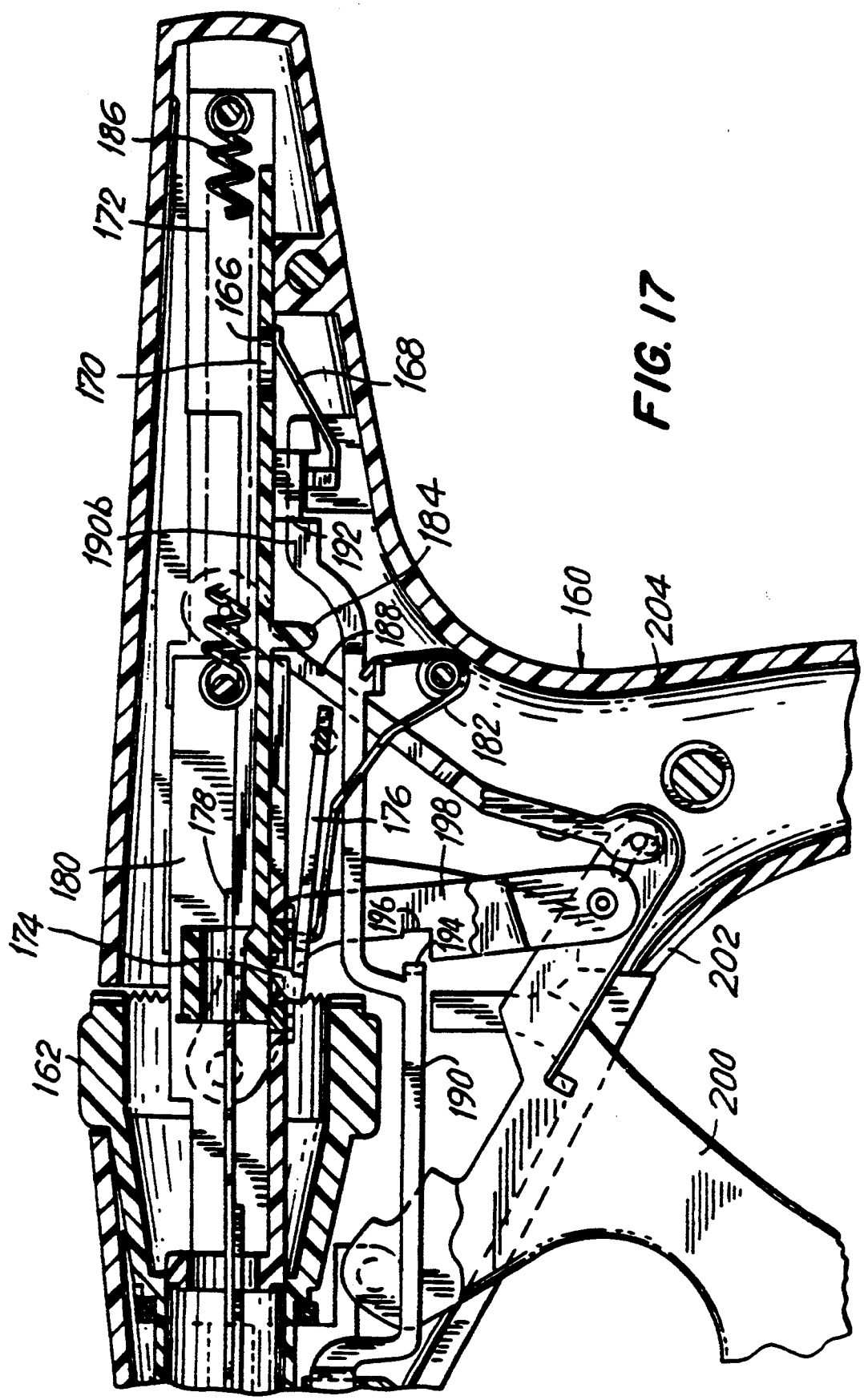
FIG. 17 is a partial cross-sectional view of the handle section of the clip applier of FIG. 16, illustrating the interfering device disengaged from the actuating and transmission system.

Referring now to FIGS. 16-18, a handle section 160 having a pistol grip structure and configuration and incorporating an interfering system is shown. Pistol grip handle section 160 controls the operation of endoscopic section 14 in a substantially similar manner as the above-mentioned palm grip handle section. The operation and structure of the pistol grip handle section and its interaction with the endoscopic section are described in more detail in U.S. Pat. No. 5,084,057 mentioned previously. In particular, the endoscopic section is preferably maintained in a rotational alignment with respect to the pistol grip handle section so that rotational movement of wheel 162 is transferred to the endoscopic section.

Referring to FIG. 17, the general operation of the first and second transmission mechanisms will be discussed. It should be noted that the overall function of the first and second transmission mechanisms to be discussed are substantially similar to the first and second transmission mechanisms discussed for the palm grip handle section. However, the following general overview will focus on the internal mechanisms and functions which may differ from the palm grip handle section.

Initially, the endoscopic clip applier is provided in the locked position, i.e., there is no clip loaded between the jaws of the endoscopic section. At this point the jaws are biased open and are free to cam between the open and closed positions. This facilitates insertion of the endoscopic section into an endoscopic tube or into the body since the jaws can cam partially closed, thereby avoiding interference with the positioning of the instrument. In this configuration, release trigger 164 is in its distal-most position, while catch 166 of pusher release leaf spring 168 engages aperture 170 of pusher drive member 172 (i.e., the first transmission mechanism), and catch 174 of latch plate 176 is biased into engagement with aperture 178 of channel drive member 180 (i.e., the second transmission mechanism) in response to spring 182. As a result, squeezing of handle 184 is prevented by the engagement of catch 174 of latch plate 176 and aperture 178 of channel drive member 180, prior to advancing a clip in position the jaws of the endoscopic section.

This configuration permits pusher leaf spring 168 to retain the pusher drive member in position against the force of the mainspring 186. Release of catch 166 of pusher release leaf spring 168 is accomplished by proximal movement of release lever 190 via finger activated trigger 164 (shown in FIG. 16). Release of catch 174 is accomplished by the engagement of the latch plate 176 by camming pin 184 extending downwardly from pusher drive member 172, when the pusher drive member moves distally under action of mainspring 186.

Referring now to FIGS. 17 and 18, the pistol grip interfering device includes tab 194 positioned on release lever 190. Preferably, tab 194 extends substantially perpendicular to the longitudinal axis of release lever 190 and is positioned on release lever 190 adjacent to notch 196 in channel link 198, as shown in FIG. 17. As noted above, release lever 190 is slidably positioned within handle section 160, having distal end 190a secured to pusher release trigger 164 and proximal end 190b adapted to slidably engage pusher release leaf spring 168. In this configuration, longitudinal movement of release lever 190 in a proximal direction causes tab 194 to engage notch 196 of channel link 198 so as to prevent actuation of handle 200 by preventing motion of channel links 198 and 202 for a period of time sufficient to allow the surgical clip to be completely positioned between the jaws of endoscopic section 14.

It should be noted that above-described interfering device for the pistol grip handle section, represents the preferred embodiment for preventing simultaneous advancement of clips into the jaws and closing of the jaws in the event the operator actuates both systems simultaneously.

The operation of the interfering device of the present invention as well as the other mechanisms within the pistol grip handle section will now be discussed with reference to FIGS. 17–21. FIG. 17 is a cross-sectional view of the pistol grip handle section 160, illustrating pusher drive member 172 in the proximal-most position, i.e., the position where the nose of the pusher bar is just proximal of the next clip in the clip array, ready to advance the clip distally into the jaws of the endoscopic section. With pusher drive member 178 in the proximal position, downwardly extending camming pin 184 has moved out of engagement with latch plate 176 thereby permitting catch 174 to enter aperture 178 of channel drive member 180 and prevent distal movement of the channel drive member. This condition locks handle 200 in the distal position whereby squeezing the handle toward hand grip 204 is prevented.

Referring now to FIGS. 19 and 20, the operation of the interfering device for pistol grip handle section 160 and the actuation of pusher drive member 172 will now be discussed. As noted above, initially pusher drive member 172 is in its proximal position and channel drive member 180 is latched by catch 174. Proximal movement of release trigger 164 causes the proximal end 190b of release lever 190 to engage leaf spring 168 so as to release catch 166 from aperture 170 in pusher drive member 172, as shown in FIG. 19. As a result, pusher drive member 172 moves distally under the action of mainspring 186 thereby, through interaction with the pusher bar within the endoscopic section, loading a clip between the jaws of the endoscopic section. Distal movement of pusher drive member 172 also causes camming pin 184 to engage latch plate 176 so as to disengage catch 174 from aperture 178 in channel drive member 180, as shown in FIG. 20. Return of release trigger 164 to its distal position enables activation of channel drive member 180 by squeezing handle 200 towards handgrip 204.

Interfering device (or tab) 194 is activated simultaneously with the distal movement of release trigger 164 and engages notch 196 in channel link 198, so as to inhibit motion of channel links 198 and 202 and prevent actuation of channel drive member 180 until tab 194 moves distally in response to the return of release trigger 164 to its normal position.

Referring now to FIG. 21, a cross-sectional view of the pistol grip handle section 160 is shown after the crimping action has taken place on a clip positioned between the jaws of the endoscopic section. In the cross-section shown in FIG. 21, pusher drive member 172 is in the proximal-most position and channel drive member 180 is in the distal-most position so that the crimping channel and the channel bracket of the endoscopic section are in the distal-most position. Proximal motion of pusher drive member 172 enables catch 166 of spring 168 to re-engage aperture 170 in pusher drive member 172 and positions the nose of the pusher bar within the endoscopic section just proximal to the next clip in the clip array for subsequent advancement of the clip distally into the jaws of the endoscopic section, as explained above. When channel drive member 180 is in its distal-most position, the camming surface of channel link 198 will prevent proximal travel of release lever 190 by blocking the path of tab 194 thus preventing release of pusher drive member 172 until channel drive member 180 returns to its normal position.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. An actuating handle for attachment to an endoscopic portion of an endoscopic surgical instrument, which comprises:
   a frame;
   a pusher drive member positioned within said frame and movable between proximal and distal positions;
   a spring member positioned within said frame and operatively connected to bias said pusher drive member toward said distal position;
   a first actuating member at least partially extending from said frame, and configured and adapted to cooperate with said pusher drive member such that actuation of said first actuating member causes said pusher drive member to move distally under the bias of said spring member;
   a second actuating member at least partially extending from said frame and movable between non-actuated and actuated positions, said second actuating member being operatively connected to a channel drive member slidably positioned within said frame and movable between proximal and distal positions; and
   means at least partially connected to said first actuators member for preventing substantial movement of said second actuating member from said non-actuated position to said actuated position until said pusher drive member is in said distal position.

2. The actuating handle according to claim 1, wherein said means for preventing substantial movement of said second actuating member comprises a rigid member having a first end connected to said first actuating member and a free second end which upon actuation of said first actuating member engages at least a portion of said second actuating member to prevent said movement of said second actuating member.

3. The actuating handle according to claim 1, wherein said first actuating member comprises a button.

4. The actuating handle according to claim 1, wherein said first actuating member comprises a trigger.

5. The actuating handle according to claim 1, wherein said second actuating member comprises a handle pivotally connected to said frame and at least one link connected between said handle and said channel drive member such that movement of said handle is translated to movement of said channel drive member.

6. The actuating handle according to claim 5, wherein said means for preventing substantial movement of said second actuating member engages said at least one link so as to prevent said movement of said second actuating member.

7. The actuating handle according to claim 1 further comprising:
means positioned within said frame for releasably maintaining said pusher drive member in said proximal position; and
means positioned within said frame and operatively connected to said first actuating member for releasing said means for releasably maintaining said pusher drive member.

8. The actuating handle according to claim 1 further comprising:
means positioned within said frame for releasably maintaining said channel drive member in said proximal position; and
means positioned within said frame for releasing said means for releasably maintaining said channel drive member.

9. The actuating handle according to claim 8, wherein said releasing means is operatively connected to said pusher drive member such that movement of said pusher drive member to said distal position causes said means for releasably maintaining said channel drive member to release said channel drive member.

* * * * *